(12) United States Patent
Buschle et al.

(10) Patent No.: US 8,784,837 B2
(45) Date of Patent: *Jul. 22, 2014

(54) VACCINES COMPRISING AN IMMUNOSTIMULATORY PEPTIDE AND AN IMMUNOSTIMULATORY OLIGODEOXYNUCLEIC ACID MOLECULE

(75) Inventors: Michael Buschle, Perchtoldsdorf (AT); André Habel, Vienna (AT); Jörg Fritz, Vienna (AT); Karin Prinz, Rehberg (AT); Karen Lingnau, Vienna (AT)

(73) Assignee: Valneva Austria GmbH, Vienna (AU)

( * ) Notice: Subject to any disclaimer, the term of this patent is extended or adjusted under 35 U.S.C. 154(b) by 49 days.

This patent is subject to a terminal disclaimer.

(21) Appl. No.: 12/759,318

(22) Filed: Apr. 13, 2010

(65) Prior Publication Data

US 2010/0297170 A1 Nov. 25, 2010

Related U.S. Application Data

(63) Continuation of application No. 10/550,754, filed as application No. PCT/EP2004/003002 on Mar. 22, 2004, now Pat. No. 7,704,514.

(30) Foreign Application Priority Data

Mar. 24, 2003 (EP) .................................... 03450072
Apr. 11, 2003 (EP) .................................... 03450084
Jul. 11, 2003 (EP) .................................... 03450171

(51) Int. Cl.
A61K 39/00 (2006.01)
A61K 39/12 (2006.01)
A61K 39/29 (2006.01)
C07K 14/005 (2006.01)

(52) U.S. Cl.
USPC .................. 424/204.1; 424/227.1; 424/228.1

(58) Field of Classification Search
None
See application file for complete search history.

(56) References Cited

U.S. PATENT DOCUMENTS

| | | | |
|---|---|---|---|
| 5,663,153 A | 9/1997 | Hutcherson et al. | 514/44 |
| 5,683,864 A | 11/1997 | Houghton et al. | 435/5 |
| 5,723,335 A | 3/1998 | Hutcherson et al. | 435/375 |
| 6,037,135 A | 3/2000 | Kubo et al. | 435/7.24 |
| 6,150,087 A | 11/2000 | Chien | 435/5 |
| 6,413,517 B1 | 7/2002 | Sette et al. | 424/185.1 |
| 6,544,518 B1 * | 4/2003 | Friede et al. | 424/184.1 |
| 7,148,191 B2 | 12/2006 | Egyed et al. | 514/2 |
| 7,704,514 B2 * | 4/2010 | Buschle et al. | 424/278.1 |
| 2002/0136776 A1 * | 9/2002 | Fang et al. | 424/501 |
| 2003/0162738 A1 | 8/2003 | Egyed et al. | 514/44 |
| 2010/0297170 A1 * | 11/2010 | Buschle et al. | 424/202.1 |

FOREIGN PATENT DOCUMENTS

| | | |
|---|---|---|
| AT | 805/2001 | 5/2000 |
| AT | 1973/2000 | 11/2000 |
| EP | 0 468 520 | 1/1992 |
| WO | WO 92/03458 | 3/1992 |
| WO | WO 93/00365 | 1/1993 |
| WO | WO 94/20127 | 9/1994 |
| WO | WO 94/25601 | 11/1994 |
| WO | WO 95/12766 | 5/1995 |
| WO | WO 95/22317 | 8/1995 |
| WO | WO 95/25122 | 9/1995 |
| WO | WO 95/27733 | 10/1995 |
| WO | WO 95/27901 | 10/1995 |
| WO | WO 96/02555 | 2/1996 |
| WO | WO 97/30721 | 8/1997 |
| WO | WO 98/15287 | 4/1998 |
| WO | WO 98/16247 | 4/1998 |
| WO | WO 98/18810 | 5/1998 |
| WO | WO 98/37919 | 9/1998 |
| WO | WO 98/40100 | 9/1998 |
| WO | WO 98/52581 | 11/1998 |
| WO | WO 98/52962 | 11/1998 |
| WO | WO 99/15259 | 4/1999 |
| WO | WO 99/33488 | 6/1999 |
| WO | WO 99/38528 | 8/1999 |
| WO | WO 99/51259 | 10/1999 |
| WO | WO 99/56755 | 11/1999 |
| WO | WO 99/63941 | 12/1999 |
| WO | WO 00/11186 | 3/2000 |
| WO | WO 00/23105 | 4/2000 |
| WO | WO 00/31542 | 6/2000 |
| WO | WO 00/44775 | 8/2000 |
| WO | WO 01/17551 | 3/2001 |
| WO | WO 01/21189 | 3/2001 |
| WO | WO 01/24822 | 4/2001 |
| WO | WO 01/54719 | 8/2001 |
| WO | WO 01/72782 | 10/2001 |
| WO | WO 01/78767 | 10/2001 |
| WO | WO 01/93903 | 12/2001 |
| WO | WO 01/93905 | 12/2001 |
| WO | WO 02/13857 | 2/2002 |

(Continued)

OTHER PUBLICATIONS

Dorland's Medical Dictionary for Healthcare Consumers (no date) (http://www.mercksource.com/pp/us/cns/cns_hl_dorlands_split.jsp?pg=/ppdocs/us/common/dorlands/dorland/four/000053439.htm).*
Stedman's Online Medical Dictionary (http://www.stedmans.com/section.cfm/45) (no date).*
Sequence alignment of SEQ ID Nos: 22 and 23 with GenEmbl database AX755047 from Lingnau et al. (WO 02095027). 2002.*

(Continued)

*Primary Examiner* — Shanon A Foley
(74) *Attorney, Agent, or Firm* — Wolf, Greenfield & Sacks, P.C.

(57) ABSTRACT

The invention refers an improved vaccine against infections with pathogens, especially viral pathogens, comprising an antigen, a peptide of the formula $R_1$—$XZSZ_N$—$XZX$—$R_2$ and an immunostimulatory deoxynucleic acid containing deoxyinosine and/or deoxyuridine residues.

18 Claims, 14 Drawing Sheets

(56) References Cited

FOREIGN PATENT DOCUMENTS

| | | |
|---|---|---|
| WO | WO 02/32451 | 4/2002 |
| WO | WO 02/33127 | 4/2002 |
| WO | WO 02/053184 | 7/2002 |
| WO | WO 02/053185 | 7/2002 |
| WO | WO 02/095027 | 11/2002 |
| WO | WO 03/047602 | 6/2003 |
| WO | WO 03/073097 | 9/2003 |
| WO | WO 2004/014936 | 2/2004 |
| WO | WO 2004/024182 | 3/2004 |

OTHER PUBLICATIONS

Franco et al. (World Journal of Hepatology. Mar. 2012; 4 (3): 74-80).*
Dorner et al. (Methods. 2013: 549-257).*
Houghton (Immunological Reviews. 2011; 239: 99-108).*
Chu et al., CpG oligodeoxynucleotides act as adjuvants that switch on T helper 1 (Th1) immunity. J Exp Med. Nov. 17, 1997;186(10):1623-31.
McCluskie et al., Route and method of delivery of DNA vaccine influence immune responses in mice and non-human primates. Mol Med. May 1999;5(5):287-300.
"Aluminiumhydroxide," Röempp, 10$^{th}$ Ed., pp. 139-140, 2006 (in German).
Aichinger et at., "Major histocompatibility complex class II-dependent unfolding, transport, and degradation of endogenous proteins," *J. Biol. Chem.*, 272:29127-29136, 1997.
Anthony et al., "Comprehensive determinant mapping of the hepatitis C-specific CD8 cell repertoire reveals unpredicted immune hierarchy," *Clinical Immunology*, 103(3):264-276, 2002.
Battegay et al., "Patients with chronic hepatitis C have circulating cytotoxic T cells which recognize hepatitis C virus-encoded peptides binding to HLA-A2.1 molecules," *J. Virol.*, 69(4):2462-2470, 1995.
Bellentani et al., "Epidemiology of hepatitis C virus infection in Italy: the slowly unraveling mystery," *Microbes Infect.*, 2(14):1757-63, 2000.
Bihl et al., "Impact of HLA-B alleles, epitope binding affinity, functional avidity, and viral coinfection on the immunodominance of virus-specific CTL responses," *J. Immunol.*, 176:4094-4101, 2006.
Bitmansour et al., "Clonotypic structure of the human CD4+ memory T cell response to cytomegalovirus," *J Immunol*, 167:1151-1163, 2001.
Blake et al., "Use of combinatorial peptide libraries to construct functional mimics of tumor epitopes recognized by MHC class I-restricted cytolytic T lymphocytes," *J. Exp. Med*, 184:121-130, 1996.
Britt and Alford, "Cytomegalovirus," In: *Fields Virology* by Fields et al. eds., Livincott-Raven, 2493-2523 1999.
Brooks et al., "HLA-B27 subtype polymorphism and CTL epitope choice: studies with EBV peptides link immunogenicity with stability of the B27:peptide complex," *J. Immunol.*, 161:5252-5259, 1998.
Bullock et al. "Initiation codon scanthrough verses termination codon readthrough demonstrates strong potential for MHC class I restricted cryptic epitope expression," *Journal of Experimental Medicine*, 186:1051-1058, 1997.
Chang et al., "Identification of HLA-A3 and -B7-restricted CTL response to hepatitis C virus in patients with acute and chronic hepatitis C," *J. Immunol.*, 162:1156-1164, 1999.
Chen et al., A novel influenza A virus mitochondrial protein that induces cell death,: *Nature Medicine*, 7:1306-1312, 2001.
Chen et al., "Efficient class II major histocompatibility complex presentation of endogenously synthesized hepatitis C virus core protein by Epstein-Bar virus-transformed B-lymphoblastoid cell lines to CD4+T cells," *Journal of Virology*, 72(10):8301-8308, 1998.
Cho et al., "Activation of human neutrophils by a synthetic antimicrobial peptide, KLKLLLLLK-NH2, via cell surface calreticulin,"*Eur. J. Biochem.*, 266:878-885, 1999.
Cox et al., "Identification of a peptide recognized by five melanoma-specific human cytotoxic t cell lines," *Science*, 264:716-719, 1994.

Di Bisceglie et al., "New therapeutic strategies for hepatitis C," *Hepatology*, 35:224-231, 2002.
Diepolder et al., "Immunodominant CD4+ T-cell epitope within nonstructural protein 3 in acute hepatitis C virus infection," *J. Virol.*, 71(8):6011-6019, 1997.
Drew and Lalezari, "Cytomegalovirus: disease syndromes and treatment," *Curr Clin Top Infect Dis*, 19:16-29, 1999.
Duenas-Carrera et al., "Enhancement of the immune response generated against hepatitis C virus envelope proteins after DNA vaccination with polyprotein-encoding plasmids," *Biotechnol. Appl. Biochem.*, 35:205-212, 2002.
Elliot et al. "Recognition of out-of-frame major histocompatibility complex class I-restricted epitopes in vivo," *European Journal of Immunology*, 26:1175-1179, 1996.
Farci and Purcell, "Clinical significance of hepatitis C virus genotypes and quasispecies," *Semin Liver Dis.*, 20(1):103-26, 2000.
Field, "Human cytomegalovirus: challenges, opportunities and new drug development," *Antiviral Chem. Chemotherapy*, 10:219-232, 1999.
Fleckenstein et al., "New ligands binding to the human leukocyte antigen class II molecule DRB+0101 based on the activity pattern of an undecappetide library," *European Journal of Biochemistry*, 240:71-77, 1996.
Fowler et al., "The outcome of congenital cytomegalovirus infection in relation to maternal antibody status," *New Engl. J. Med.*, 326:663-673, 1992.
Gallot et al., "Purification of Ag-specific T lymphocytes after direct peripheral blood mononuclear cell stimulation followed by CD25 selection. I. Application to CD4(+) or CD8(+) cytomegalovirus phosphoprotein pp65 epitope determination," *J. Immunol.*, 167:4196-4206, 2001.
Gavin et al., "Alkali hydrolysis of recombinant proteins allows for the rapid identification of class I MHC-restricted CTL epitopes," *J. Immunol.*, 151:3971-3980, 1993.
Gorga et al., "Purification and characterization of class II histocompatibility antigens from a homozygous human B cell line," *J Biol. Chem.*, 262:16087-16094, 1987.
Greenberg and Riddell, "Deficient Cellular Immunity—Finding and Fixing the Defects," *Science*, 285:546-551, 1999.
Greten and Schneck, "Development and use of multimeric major histocompatibility complex molecules," *Clinical and Diagnostic Laboratory Immunology*, 9(2):216-220, 2002.
Gruener et al., "Sustained dysfunction of antiviral CD8+ T lymphocytes after infection with hepatitis C virus," *J. Virol.*, 75:5550-5558, 2001.
Hammer et al., "Promiscuous and allel-specific anchors in HLA-DR-binding peptides," *Cell*, 74:197-203, 1993.
Heemels and Ploegh, "Generation, translocation and presentation of mhc class I-restricted peptides," *Annu Rev Biochem*, 64:463-491, 1995.
Heile et al., "Evaluation of hepatitis C virus glycoprotein E2 for vaccine design: an endoplasmic reticulum-retained recombinant protein is superior to secreted recombinant protein and DNA-based vaccine candidates," *J. Virol.*, 74(15):6885-6892, 2000.
Hemmer et al., "Predictable TCR antigen recognition based on peptide scans leads to the identification of agonist ligands with no sequence homology," *J. Immunol.*, 160:3631-3636, 1998.
Hemmer et al., "The use of soluble synthetic peptide combinatorial libraries to determine antigen recognition of T cells," *J. Peptide Res.*, 52:338-345, 1998.
HLA-prevalence studies, In: HLA 1998, (Gjertson and Terasaki, eds.) American Society for Histocompatibility and Immunogenetics, Lenexa, Kansas, pp. 103-263, 1998.
Hoffmann et al., "Mapping of Immunodominant CD4+ T Lymphocyte Epitopes of Hepatitis C Virus Antigens and Their Relevance During the Course if Chronic Infection," *Hepatology*, 21(3):632-638, 1995.
Hunziker et al, "In vitro studies of core peptide-bearing immunopotentiating reconstituted influenza virosomes as a non-live prototype vaccine against hepatitis C virus," *International Immunology*, 14(6):615-626, 2002.

(56) References Cited

OTHER PUBLICATIONS

Ibe et al., "Identification and characterization of a cytotoxic T cell epitope of hepatitis C virus presented by HLA-B*3501 in acute hepatitis," *J. Gen. Virol.*, 79:1735-1744, 1998.
Inchauspe and Feinstone, "Development of a hepatitis C virus vaccine," *Clinics in Liver Disease*, 7:243-259, 2003.
Keilholz et al., "Immunologic monitoring of cancer vaccine therapy: results of a workshop sponsored by the Society for Biological Therapy," *J Immunother.*, 25(2):97-138, 2002.
Kern et al., "Analysis of cd8 t cell reactivity to cytomegalovirus using protein-spanning pools of overlapping pentadecapeptides," *Eur J Immun*, 30:1676-1682, 2000.
Kern et al., "Target structures of the cd8+-t-cell response to human cytomegalovirus: the 72-kilodalton major immediate-early protein revisited," *J Virol*, 73:8179-8184, 1999.
Khattab et al., "Three T-cell epitopes within the C-terminal 265 amino acids of the matrix protein pp65 of human cytomegalovirus recognized by human lymphocytes," *J. Med. Virol.*, 52:68-76, 1997.
Klein, *Natural History of the MHC*, John Wiley and Sons, 1986.
Komanduri et al., "Restoration of cytomegalovirus-specific cd4+t-lymphocyte responses after ganciclovir and highly active antiretroviral therapy in individuals infected with HIV-1," *Nat Med*, 4:953-956, 1998.
Koziel et al., "Hepatitis C virus (HCV)-specific cytotoxic T lymphocytes recognize epitopes in the core and envelope proteins of HCV," *J. Virol.*, 67:7522-7532, 1993.
Koziel et al., "HLA class I-restricted cytotoxic T lymphocytes specific for hepatitis C virus. Identification of multiple epitopes and characterization of patterns of cytokine release," *J. Clin. Invest.*, 96:2311-2321, 1995.
Kronenberg et al., "Conserved lipid and peptide presentation functions of nonclassical class I molecules," *Immunol. Today*, 20:515-521, 1999.
Kurokohchi et al., "A novel cytotoxic T-cell epitope presented by HLA-A24 molecule in hepatitis C virus infection," *J. Hepatology*, 34:930-935, 2001.
Kuzushima et al., "Efficient Identification of HLA-A*2402-restricted cytomegalovirus-specific CD8+T-cell epitopes by a computer algorithm and an enzyme-linked immunospot assay," *Blood*, 98:1872-1880, 2001.
Kwok et al., "Rapid epitope identification from complex class-II-restricted T-cell antigens," *Trends in Immunology*, 22(11):583-588, 2001.
Lalvani et at, "Rapid effector function in CD8+ memory T cells," *J. Exp. Med.*, 186:859-865, 1997.
Lamas et al., "Relationship between peptide binding and T cell epitope selection: a study with subtypes of HLA-B27," *Int. Immunol.*, 10:259-266, 1998.
Lamonaca et al., "Conserved Hepatitis C Virus Sequences Are Highly Immunogenic for CD4+T Cells: Implications for Vaccine Development," *Hepatology*, 30(4):1088-1098, 1999.
Lauer et al., "Comprehensive analysis of CD8+-T-cell responces against hepatitis C virus reveals multiple unpredicted specificities," *Journal of Virology*, 76(12):6104-6113, 2002.
Lechmann and Liang, "Vaccine development for hepatitis C," *Seminars in Liver Disease*, 20:211-226, 2000.
Leroux-Roels et al., "Lymphoproliferative Responses to Hepatitis C Virus Coes, E1, E2, and NS3 in Patients With Chronic Hepatitis C Infection Treated With Interferon Alfa," *Hepatology*, 23(1):8-16, 1996.
Levitsky et al., "Supermotif Peptide Binding and Degeneracy of MHC: Peptide Recognition in an EBV Peptide-Specific CTL Response with Highly Restricted TCR Usage," *Human Immunol.*, 61:972-984, 2000.
Liang et al., "Pathogeneis, Natural History, Treatment, and Prevention of Hepatitis C," *Ann Intern Med.*, 132(4):296-305, 2000.
Maecker et al., "Use of overlapping peptide mixtures as antigens for cytokine flow cytometry," *J Immunol Methods*, 255:27-40, 2001.
Malarkannan et al., "Presentation of out-of-frame peptide/MHC class I complexes by a novel translation initiation mechanism," *Immunity*, 10:681-690, 1999.
Masuoka et al., "Identification of the HLA-A24 peptide epitope within cytomegalovirus protein pp65 recognized by CMV-specific cytotoxic T lymphocytes," *Viral Immunology*, 14:369-377, 2001.
Maynard et al. "An alternative translation reading frame encodes an immunodominant retroviral CTL determinant expressed by an immunodeficiency-causing retrovirus," *J. of Immunology*, 160:39-50, 1998.
Maynard et al. "Non-traditionally derived CTL epitopes: exceptions that prove the rules?" *Immunology Today*, 19:551-556, 1998.
McCluskie et al., "Parenteral and mucosal prime-boost immunization strategies in mice with hepatitis B surface antigen and CpG DNA," *Fems Immunol and Medical Microbiol*, 32:179-185, 2002.
McLaughlin-Taylor et al., "Identification of the major late human cytomegalovirus matrix protein pp65 as a target antigen for CD8+ virus-specific cytotoxic T lymphocytes," *J. Med. Virol.*, 43:103-110, 1994.
Morgan et al., "The influence of exogenous peptide on beta2-microglobulin exchange in the HLA complex: analysis in real time," *Immunogenetics*, 48:98-107, 1998.
Nakajima et al., "Chemotherapeutic activity of synthetic antimicrobial peptides: correlation between chemotherapeutic activity and neutrophil-activating activity," *FEBS Lett.*, 415:64-66, 1997.
Nichols and Boeckh, "Recent advances in the therapy and prevention of CMV infections," *J. Clin. Virol.*, 16:25-40, 2000.
Nijman et al., "Identification of peptide sequences that potentially trigger HLA-A2.1-restricted cytotoxic T lymphocytes," *Eur. J. Immunol.*, 6:1215-1219, 1993.
Novak et al., "Tetramer-guided epitope mapping: rapid identification and characterization of immunodominant CD4+T cell eiptopes from complex antigens," *The Journal of Immunology*, 166:6665-6670, 2001.
Office Action, issued in Japanese Application No. 2006-504798, mailed Mar. 2, 2010 (English Translation).
Office Communication, issued in U.S. Appl. No. 10/550,754, mailed Jan. 6, 2009.
Office Communication, issued in U.S. Appl. No. 10/550,754, mailed Jul. 1, 2008.
Office Communication, issued in U.S. Appl. No. 10/550,754, mailed Mar. 24, 2008.
Parker et al., "Scheme for ranking potential HLA-A2 binding peptides based on independent binding of individual peptide side-chains," *J. Immunol.*, 152:163, 1994.
Plotkin, "Vaccination against cytomegalovirus, the changeling demon," *Pediatr Infect Dis J*, 18:313-325, 1999.
Rammensee et al., "SYFPEITHI: database for MHC ligands and peptide motifs," *Immunogenetics*, 50:213-219, 1999.
Reddehase, "The immunogenicity of human and murine cytomegaloviruses," *Curr Opin Immunol*, 12:390-396, 2000.
Rehermann et al., "Differential cytotoxic T-lymphocyte responsiveness to the hepatitis B and C viruses in chronically infected patients," *J. Virol.*, 70(10):7092-7102, 1996.
Retriere et al., "Generation of cytomegalovirus-specific human T-lymphocyte clones by using autologous B-lymphoblastoid cells with stable expression of pp65 or IE1 proteins: a tool to study the fine specificity of the antiviral response," *J. Virol.*, 74:3948-3952, 2000.
Rollier et al., "Control of heterologous hepatitis C virus infection in chimpanzees is associated with the quality of vaccine-induced peripheral T-helper immune response," *J. Virol.*, 78(1):187-196, 2004.
Sarobe et al., "Enhanced in vitro potency and in vivo immunogenicity of a CTL epitope from hepatitis C virus core protein following amino acid replacement at secondary HLA-A2.1 binding positions," *J. Clin. Invest.*, 102(6):1239-1248, 1998.
Saulquin et al., "A global appraisal of immunodominant CD8 T cell responses to Epstein-Barr virus and cytomegalovirus by bulk screening," *Eur. J. Immunol.*, 30:2531-2539, 2000.
Shastri et al., "Major histocompatibility class I molecules can present cryptic translation products to T-cells.," *J. Biol. Chem.* 270:1088-1091, 1995.

(56) References Cited

OTHER PUBLICATIONS

Shirai et al., "An epitope in hepatitis C virus core region recognized by cytotoxic T cells in mice and humans," *J. Virol.*, 68(5):3334-3342, 1994.

Sia and Patel, "New strategies for prevention and therapy of cytomegalovirus infection and disease in solid-organ transplant recipients," *Clin. Microbiol. Rev.*, 13:83-121, 2000.

Smith et al., "Peptide sequences binding to MHC class II proteins," *Molecular Immunology*, 31:1431-1437, 1994.

Solache et al., "Identification of three HLA-A*0201-restricted cytotoxic T cell epitopes in the cytomegalovirus protein pp65 that are conserved between eight strains of the virus," *J. Immunol.*, 163:5512-5518, 1999.

Stern and Wiley, "Antigenic peptide binding by class I and class II histocompatibility proteins," *Structure*, 2:245-251, 1994.

Stevens et al., "Efficient generation of major histocompatibility complex class I-peptide complexes using synthetic peptide libraries," *Journal of Biological Chemistry*, 273:2874-2884, 1998.

Sturniolo et al., "Generation of tissue-specific and promiscuous HLA ligand databases using DNA microarrays and virtual HLA class II matrices," *Nature Biotechnology*, 17:555-562, 1999.

Tana et al., "An HLA-binding-motif-aided peptide epitope library: a novel library design for the screening of HLA-DR4-restricted antigenic peptides recognized by CD4+ T cells," *J. Hum Genet*, 43:14-21, 1998.

Thursz et al., "Influence of MHC class II genotype on outcome of infection with hepatitis C virus. The HENCORE group. Hepatitis C European Network for Cooperative Research," *Lancet*, 354(9196):2119-24, 1999.

Tobery et al., "A simple and efficient method for the monitoring of antigen-specific T cell responses using peptide pool arrays in a modified elispot assay," *J Immunol Methods*, 254:59-66, 2001.

Tourdot et al., "A general strategy to enhance immunogenicity of low-affinity HLA-A2.1-associated peptides: implication in the identification of cryptic tumor epitopes," *Eur. J. Immunol.* 30:3411-3421, 2000.

Tynan et al., "The immunogenicity of a viral cytotoxic T cell epitope is controlled by its MHC-bound conformation," *J. Exp. Med.*, 202:1249-1260, 2005.

Udaka et al., "Decrypting the structure of major histocompatibility complex class I-restricted cytotoxic T lymphocyte epitopes with complex peptide libraries," *J. Exp. Med.*, 181:2097-2108, 1995.

Valli et al., "Binding of myelin basic protein peptides to human histocompatibility leukocyte antigen class II molecules and their recognition by T cells from multiple sclerosis patients," *J. Clin. Invest.*, 91:616-628, 1993.

Van den Eynde and van der Bruggen, "T cell defined tumor antigens," *Curr Opin Immunol*, 5:684-693, 1997.

Varaklioti et al., "Alternative translation occurs within the core coding region of the hepatitis C viral menome," *The Journal of Biological Chemistry*, 227:17713-17721, 2002.

Vernacchio et at, "Effect of monophosphoryl lipid A (MPL) on T-helper cells when administered as an adjuvant with pneumococcal-CRM197 conjugate vaccine in healthy toddlers," *Vaccine*, 20(31-32):3658-67, 2002.

Villadangos and Ploegh, "Proteolysis in mhc class II antigen presentation: who's in charge," *Immunity*, 12:233-239, 2000.

Von Son et al., "Overcoming the problem of cytomegalovirus infection after organ transplantation: calling for Heracles?," *Intervirology*, 42:285-290, 1999.

Waldrop et al., "Normal human cd4+ memory t cells display broad heterogeneity in their activation threshold for cytokine synthesis," *J Immunol*, 161:5284, 1998.

Walewski et al., "Evidence for a new hepatitis C virus antigen encoded in an overlapping reading frame," *RNA*, 7:710-721, 2001.

Wang et al., "Sequence variation in the gene encoding the nonstructural 3 protein of hepatitis C virus: evidence for immune selection," *J. Mol. Evol.*, 54:456-473, 2002.

Ward et al., "Cellular immune responses against hepatitis C virus: the evidence base 2002," *Clin Exp Immunol.*, 128(2):195-203, 2002.

Weekes et al., "Human CD28-CD28+ T cells contain greatly expanded functional virus-specific memory CTL clones," *J. Immunol*, 162:7569-7577, 1999.

Weekes et al., "The memory cytotoxic T-lymphocyte (CTL) response to human cytomegalovirus infection contains individual peptide-specific CTL clones that have undergone extensive expansion in vivo," *J. Virol.*, 73(3):2099-2108, 1999.

Weiner et al, "Persistent hepatitis C virus infection in a chimpanzee is associated with emergence of a cytotoxic T lymphocyte escape variant," *Proc Natl Acad Sci U S A.*, 92(7):2755-9, 1995.

Wentworth et al., "Identification of A2-restricted hepatitis C virus-specific cytotoxic T lymphocyte epitopes from conserved regions of the viral genome," *Int. Immunol.*, 8(5):651-659, 1996.

Wilson et al., "Immunogenicity. I. Use of peptide libraries to identify epitopes that activate clonotypic CD4+ T cells and induce T cell responses to native peptide ligands," *J. Immunol.*, 163:6424-6434, 1999.

Wolfe et al., "Isolation of naturally processed peptides recognized by cytolytic t lymphocytes(ctl) on human emlanoma cells in association with hla-a2.1," *Int. J. Cancer*, 57:413-419, 1994.

Wong et al., "Detection of diverse hepatitis C virus (HCV)-specific cytotoxic T lymphocytes in peripheral blood of infected persons by screening for responses to all tranlated proteins of HCV," *Journal of Virology*, 75(3):1229-1235, 2001.

Wong et al., "Liver-derived CTL in hepatitis C virus infection: breadth and specificity of responses in a cohort of persons with chronic infection," *J. Immunol.*, 160:1479-1488, 1998.

Xu et al., "Synthesis of a novel hepatitis C virus protein by ribosomal frameshift," *The EMBO Journal*, 20:3840-3848, 2001.

Zaia et al., "Cytomegalovirus prevention and treatment in 2000," *Hematology*, 339-355, 2000.

\* cited by examiner

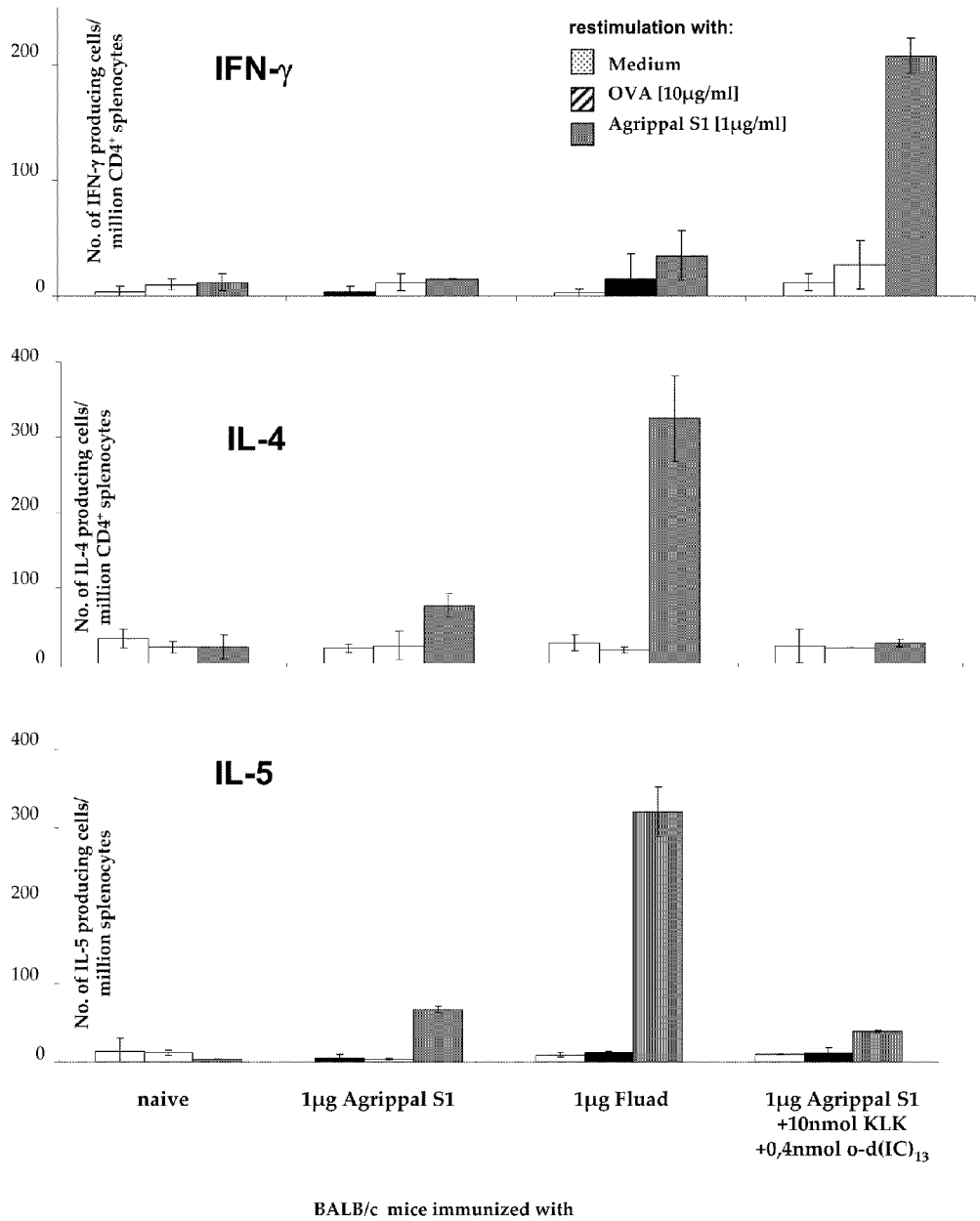

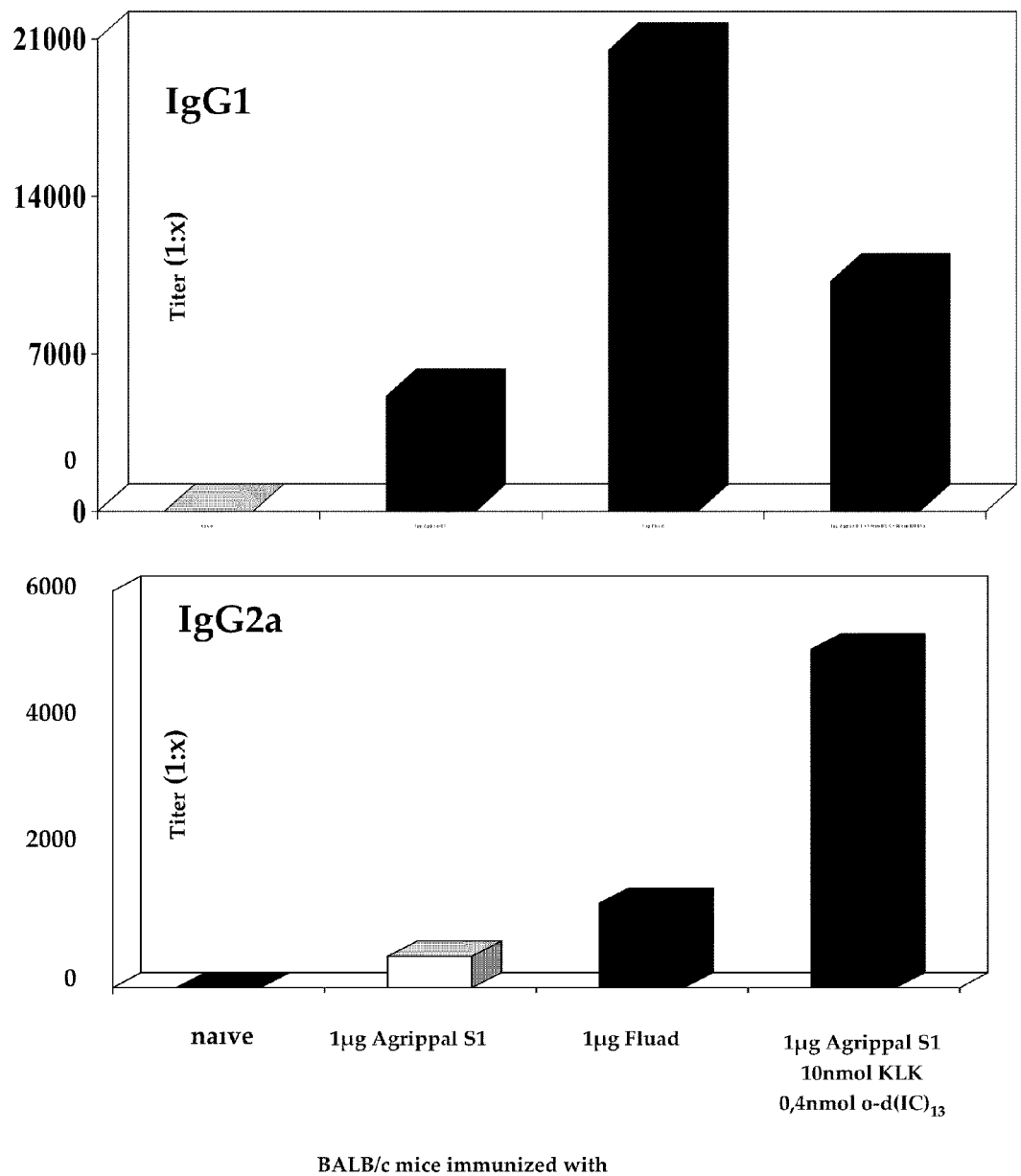

Fig. 4:

mouse sera tested against hemagglutinin derived from strain:

⊠ A/New Caledonia/20/99 (H1/N1)
▦ A/Panama/2007/99 (H3/N2)

HI Assay anti-hemagglutinin titer (1:x)

640
160
120
80
40

BALB/c mice immunized with:
- naive
- 1μg Agrippal S1
- 1μg Fluad
- 1μg Agrippal S1 10nmol KLK 0.5nmol o-d(IC)$_{13}$

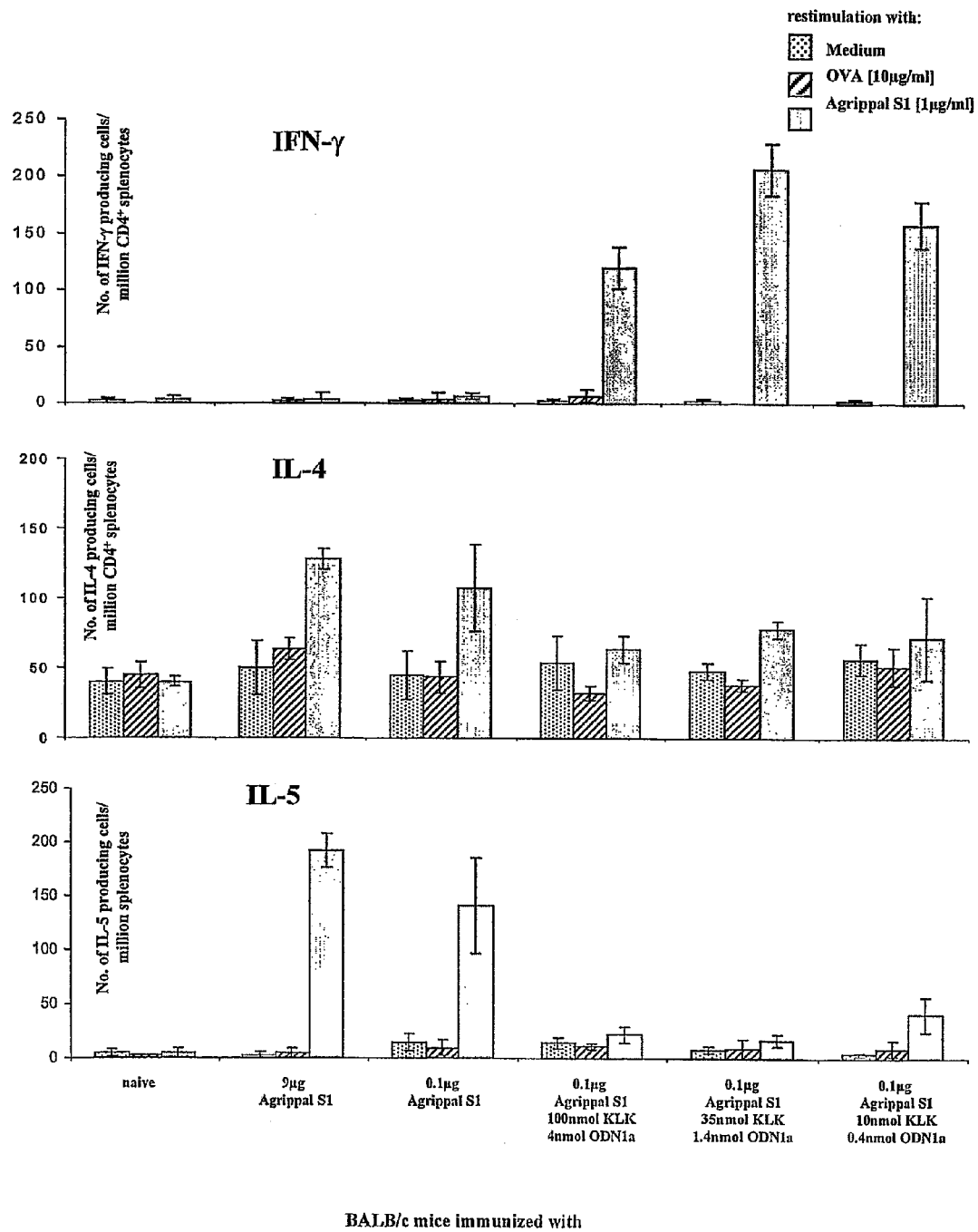

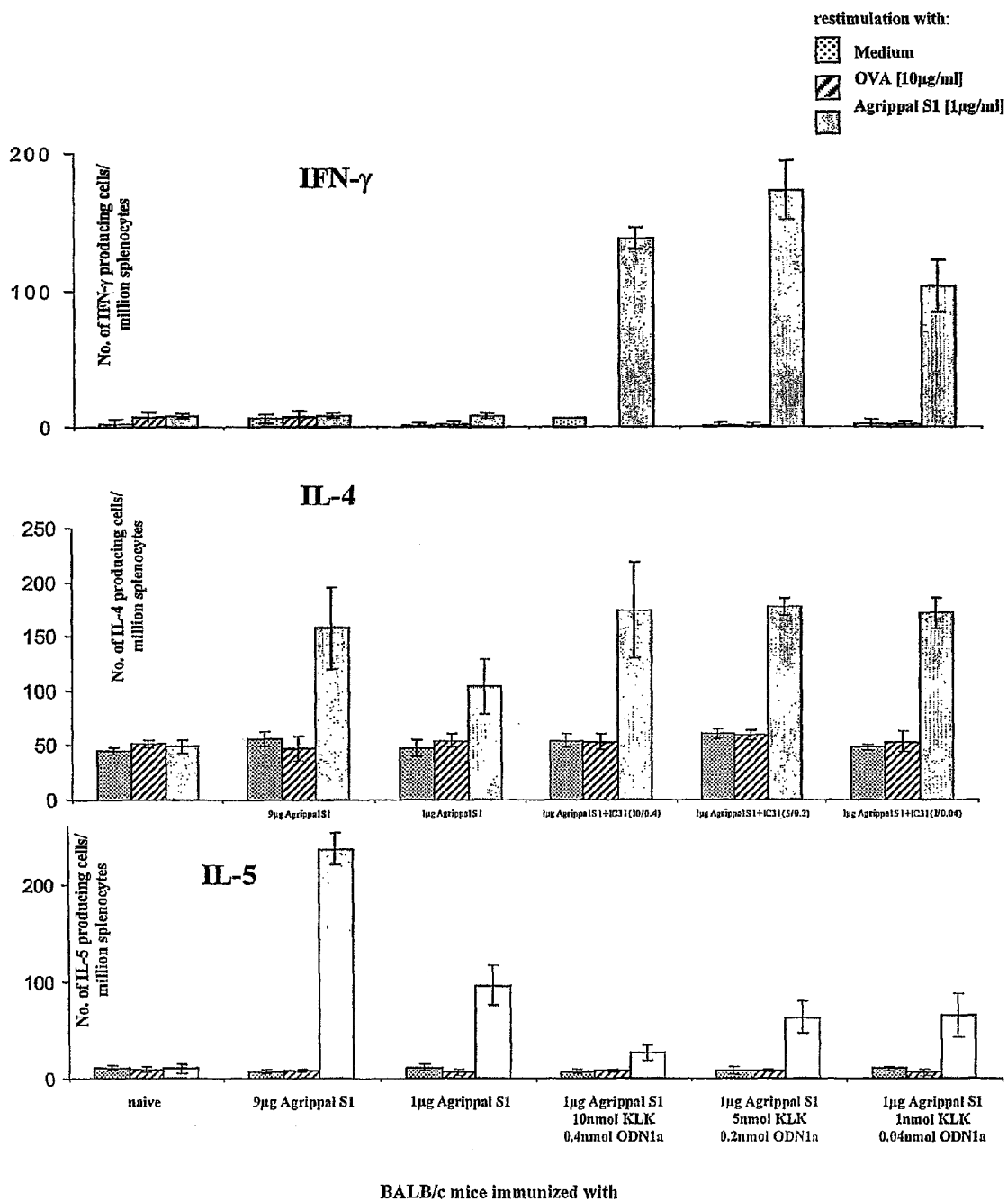

```
                        SEQUENCE LISTING

<160> NUMBER OF SEQ ID NOS: 23

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(9)
<223> OTHER INFORMATION: X = any positively charged amino acid

<400> SEQUENCE: 1

Xaa Glx Xaa Glx Glx Glx Xaa Glx Xaa
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(10)
<223> OTHER INFORMATION: X = any positively charged amino acid

<400> SEQUENCE: 2

Xaa Glx Xaa Glx Glx Glx Glx Xaa Glx Xaa
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(11)

<400> SEQUENCE: 3

Xaa Glx Xaa Glx Glx Glx Glx Glx Xaa Glx Xaa
1               5                   10
```

```
<210> SEQ ID NO 4
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(12)
<223> OTHER INFORMATION: X = any positively charged amino acid

<400> SEQUENCE: 4

Xaa Glx Xaa Glx Glx Glx Glx Glx Xaa Glx Xaa
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(13)
<223> OTHER INFORMATION: X = any positively charged amino acid

<400> SEQUENCE: 5

Xaa Glx Xaa Glx Glx Glx Glx Glx Glx Glx Xaa Glx Xaa
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 6

Lys Leu Lys Leu Leu Leu Leu Leu Lys Leu Lys
1               5                   10

<210> SEQ ID NO 7
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 7

Ile Cys Ile Cys Ile Cys Ile Cys Ile Cys Ile Cys Ile Cys Ile Cys
1               5                   10                  15

Ile Cys Ile Cys Ile Cys Ile Cys Ile Cys
            20                  25

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 8

Gly Leu Cys Thr Leu Val Ala Met Leu
1               5

<210> SEQ ID NO 9
<211> LENGTH: 10
<212> TYPE: PRT
```

```
<213> ORGANISM: Artificial Sequence
<220> FEATURE:
<223> OTHER INFORMATION: Synthetic Peptide

<400> SEQUENCE: 9

Ile Ala Ser Asn Glu Asn Met Glu Thr Met
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 10

Thr Met Leu Tyr Asn Lys Met Glu Phe
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 11

Ser Ser Ile Ala Ala Gln Asp Ala Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 12

Val Thr Ile Leu Asn Leu Ala Leu Leu
1               5

<210> SEQ ID NO 13
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 13

Lys Phe Pro Gly Gly Gly Gln Ile Val Gly Gly Val Tyr Leu Leu Pro
1               5                   10                  15

Arg Arg Gly Pro Arg Leu
            20

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 14

Gly Tyr Lys Val Leu Val Leu Asn Pro Ser Val Ala Ala Thr
1               5                   10
```

```
<210> SEQ ID NO 15
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 15

Asp Leu Met Gly Tyr Ile Pro Ala Val
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 16

Cys Ile Asn Gly Val Cys Trp Thr Val
1               5

<210> SEQ ID NO 17
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 17

His Met Trp Asn Phe Ile Ser Gly Ile Gln Tyr Leu Ala Gly Leu Ser
1               5                   10                  15

Thr Leu Pro Gly Asn Pro Ala
            20

<210> SEQ ID NO 18
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 18

Tyr Met Asp Gly Thr Met Ser Gln Val
1               5

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
tccatgacgt tcctgatgct                                            20

<210> SEQ ID NO 20
<211> LENGTH: 18
<212> TYPE: DNA
<213> ORGANISM: Artificial Sequence
<220> FEATURE:
<223> OTHER INFORMATION: Synthetic primer

<400> SEQUENCE: 20
tccatgacgt tcctgatg                                              18
```

```
<210> SEQ ID NO 21
<211> LENGTH: 26
<212> TYPE: DNA
<213> ORGANISM: Artificial sequence
<220> FEATURE:
<223> OTHER INFORMATION: oligo-d(IC)13
<220> FEATURE:
<221> NAME/KEY: misc_feature
<222> LOCATION: (1)..(26)
<223> OTHER INFORMATION: n=inosine

<400> SEQUENCE: 21
ncncncncnc ncncncncnc ncncnc                                        26

<210> SEQ ID NO 22
<211> LENGTH: 20
<212> TYPE: DNA
<213> ORGANISM: Artificial sequence
<220> FEATURE:
<223> OTHER INFORMATION: I-ODN2
<220> FEATURE:
<221> NAME/KEY: misc_feature
<222> LOCATION: (1)..(20)
<223> OTHER INFORMATION: thiophosphate substituted
<220> FEATURE:
<221> NAME/KEY: misc_feature
<222> LOCATION: (9)..(9)
<223> OTHER INFORMATION: n=inosine

<400> SEQUENCE: 22
tccatgacnt tcctgatgct                                               20

<210> SEQ ID NO 23
<211> LENGTH: 20
<212> TYPE: DNA
<213> ORGANISM: Artificial sequence
<220> FEATURE:
<223> OTHER INFORMATION: I-ODN2b
<220> FEATURE:
<221> NAME/KEY: misc_feature
<222> LOCATION: (9)..(9)
<223> OTHER INFORMATION: n=inosine

<400> SEQUENCE: 23
tccatgacnt tcctgatgct                                               20
```

VACCINES COMPRISING AN IMMUNOSTIMULATORY PEPTIDE AND AN IMMUNOSTIMULATORY OLIGODEOXYNUCLEIC ACID MOLECULE

CROSS-REFERENCE TO RELATED APPLICATIONS

This application is a continuation of U.S. application Ser. No. 10/550,754, filed Sep. 23, 2005 now U.S. Pat. No. 7,704,514, which is a national phase application under 35 U.S.C. §371 of International Application No. PCT/EP2004/003002 filed 22 Mar. 2004, which claims priority to European Patent Application No. 034500728 filed 24 Mar. 2003, European Patent Application No. 03450084.3 filed 11 Apr. 2003, and European Patent Application No. 03450171.8 filed 11 Jul. 2003. The entire text of each of the above-referenced disclosures is specifically incorporated by reference.

BACKGROUND

The present invention relates to improved vaccines, especially viral vaccines and methods of making thereof.

Host protection from invading pathogens involves cellular and humoral effectors and results from the concerted action of both non-adaptive (innate) and adaptive (acquired) immunity. The latter is based on specific immunological recognition mediated by receptors, is a recent acquisition of the immune system, and is present only in vertebrates. The former evolved before the development of adaptive immunity, consisting of a variety of cells and molecules distributed throughout the organism with the task of keeping potential pathogens under control.

B and T lymphocytes are the mediators of acquired antigen-specific adaptive immunity, including the development of immunological memory, which is the main goal of creating a successful vaccine. Antigen presenting cells (APCs) are highly specialized cells that can process antigens and display their processed fragments on the cell surface together with molecules required for lymphocyte activation. This means that APCs are very important for the initiation of specific immune reactions. The main APCs for T lymphocyte activation are dendritic cells (DCs), macrophages, and B cells, whereas the main APCS for B cells are follicular dendritic cells. In general DCs are the most powerful APCs in terms of initiation of immune responses stimulating quiescent naive and memory B and T lymphocytes.

The natural task of APCs in the periphery (e.g. DCs or Langerhans cells) is to capture and process antigens, thereby being activated they start to express lymphocyte co-stimulatory molecules, migrate to lymphoid organs, secrete cytokines and present antigens to different populations of lymphocytes, initiating antigen-specific immune responses. They not only activate lymphocytes, under certain circumstances, they also tolerize T cells to antigens.

Antigen recognition by T lymphocytes is major histocompatibility complex (MHC)-restricted. A given T lymphocyte will recognize an antigen only when the peptide is bound to a particular MHC molecule. In general, T lymphocytes are stimulated only in the presence of self MHC molecules, and antigen is recognized only as peptides bound to self MHC molecules. MHC restriction defines T lymphocyte specificity in terms of the antigen recognized and in terms of the MHC molecule that binds its peptide fragment.

Intracellular and extracellular antigens present quite different challenges to the immune system, both in terms of recognition and of appropriate response. Presentation of antigens to T cells is mediated by two distinct classes of molecules —MHC class I (MHC-I) and MHC class II (MHC-II), which utilize distinct antigen processing pathways. Mainly one could distinguish between two major antigen processing pathways that have evolved. Peptides derived from intracellular antigens are presented to $CD8^+$ T cells by MHC class I molecules, which are expressed on virtually all cells, while extracellular antigen-derived peptides are presented to $CD4^+$ T cells by MHC-II molecules. However, there are certain exceptions to this dichotomy. Several studies have shown that peptides generated from endocytosed particulate or soluble proteins are presented on MHC-I molecules in macrophages as well as in dendritic cells. Therefore APCs like dendritic cells sitting in the periphery, exerting high potency to capture and process extracellular antigens and presenting them on MHC-I molecules to T lymphocytes are interesting targets in pulsing them extracellularly with antigens in vitro and in vivo.

The important and unique role of APCs, including stimulating activity on different types of leukocytes, is reflecting their central position as targets for appropriate strategies in developing successful vaccines. Theoretically one way to do so is to enhance or stimulate their natural task, the uptake of antigen(s). Once pulsed with the appropriate antigens the vaccine is directed against, APCs should start to process the uptaken antigen(s), thereby being activated, expressing lymphocyte co-stimulatory molecules, migrating to lymphoid organs, secreting cytokines and presenting antigens to different populations of lymphocytes thereby initiating immune responses.

Activated T cells generally secrete a number of effector cytokines in a highly regulated fashion, e.g. interleukin 2 (IL-2), IL-4, IL-5, IL-10 and interferon-gamma (IFN-g). The functional detection of cytotoxic T lymphocyte responses to specific antigens (e.g. tumor antigens, in general antigens administered in a vaccine) is commonly monitored by an ELISpot assay (enzyme-linked immunospot assay), a technique analyzing cytokine production at the single cell level. In the present invention an ELISpot assay for the cellular immunity (type 1 immune response) promoting cytokine IFN-g is used to monitor successful antigen-specific T cell activation. Furthermore, the cytokine IL-4 is determined as an indicator for a type 2 response, usually involved in promoting strong humoral responses. In addition, the humoral immune response was determined by ELISA (IgG1 as indicator for a type 2 response, IgG2b as indicator for a type 1 response).

It has previously been shown that polycations efficiently enhance the uptake of MHC class I-matched peptides into tumor cells, a peptide or protein pulsing process which was called "TRANSloading". Furthermore, it has been shown that polycations are able to "TRANSload" peptides or proteins into antigen presenting cells in vivo as well as in vitro. In addition, co-injection of a mixture of poly-L-arginine or poly-L-lysine together with an appropriate peptide as a vaccine protects animals from tumor growth in mouse models. This chemically defined vaccine is able to induce a high number of antigen/peptide-specific T cells. That was shown to be at, least partly attributable to an enhanced uptake of peptides into APCs mediated by the polycation indicating that APCs when pulsed in vivo with antigens can induce T cell-mediated immunity to the administered antigen.

As opposed to adaptive immunity, which is characterized by a highly specific but relatively slow response, innate immunity is based on effector mechanisms that are triggered by differences in the structure of microbial components relative to the host. These mechanisms can mount a fairly rapid initial response, which mainly leads to neutralization of the noxious agents. Reactions of innate immunity are the only defence strategy of lower phyla and have been retained in vertebrates as a first line host defence before the adaptive immune system is mobilized.

In higher vertebrates the effector cells of innate immunity are neutrophils, macrophages, and natural killer cells and probably also dendritic cells, whereas the humoral components in this pathway are the complement cascade and a variety of different binding proteins.

A rapid and effective component of innate immunity is the production of a large variety of microbicidal peptides with a length of usually between about 12 and about one hundred amino acid residues. Several hundred different antimicrobial peptides have been isolated from a variety of organisms, ranging from sponges, insects to animals and humans, which points to a wide-spread distribution of these molecules. Antimicrobial peptides are also produced by bacteria as antagonistic substances against competing organisms.

Two major subsets of $CD4^+$ T cells (T-helper 1 (Th1) and T-helper 2 (Th2)) have been identified in mouse and human, based on their secretion of different cytokine profiles and their different effector functions. Th1 cells are mainly involved in the generation of so called type 1 immune responses, which are typically characterized by the induction of delayed-type hypersensitivity responses, cell-mediated immunity, immunoglobulin class switching to IgG2a/IgG2b and secretion of i.a. Interferon-gamma. In contrast, Th2 cells are involved in the generation of so called type 2 responses, which are characterized by the induction of humoral immunity by activating B cells, leading to antibody production including class switching to $IgG_1$ and IgE. Type 2 responses are also characterized by the secretion of the following cytokines: IL-4, IL-5, IL-6 and IL-10.

In most situations, the type of response induced (type 1 or type 2) has a significant impact on the protective efficacy of a vaccine. Alternative adjuvants tend to favour specific types of responses. However, adjuvant selection is complicated by functional unpredictabilities and also by commercial constraints and availability.

Infections with Influenza virus belong to the most important and frequent infections and has a significant mortality rate, especially for older people or people with deficiencies in the immune system. Currently, there are a number of Influenza vaccines on the market; however, not all vaccinations lead to protectivity against Influenza infections. Therefore, a need to improve current Influenza vaccines exists in order to enlarge the protection efficacy.

Moreover, since most of the current vaccines are almost exclusively eliciting type 2 responses, also a need exists to provide improved vaccines which show a type 1 directed immune response or vaccines which allow—in addition to a type 2 response—also a significant type immune reaction. Moreover, vaccines already available should be provided in an improved form which allows the induction of a type 1 response.

Therefore, the present invention provides an improved vaccine against (viral) infections comprising an antigen, a peptide of the formula $R_1$—$XZXZ_NXZX$—$R_2$ (SEQ ID NOS:1-5) and an immunostimulatory deoxynucleic acid containing deoxyinosine and/or deoxyuridine residues.

According to the experiments performed in course of the present invention, the combination of these two types of Immunizers has shown a synergistical effect with respect to antigens. This was specifically shown with respect to common Influenza antigens (especially haemagglutinin and neuraminidase) and Hepatitis virus antigens. This synergistic effect especially for viral antigens was not derivable from the known properties of these substance classes. Although each of these two substance classes is known to have excellent immunostimulating properties (WO 02/32451, WO 01/93905 and PCT/EP02/05448), the combined effect for viral pathogens, especially for Influenza and Hepatitis virus antigens, was significantly better than could be expected from the mere addition of these single efficacies.

With the present invention it is also possible to significantly improve viral vaccines, especially Influenza or Hepatitis A, B or C vaccines, being already available or on the market simply by additionally providing the combination of the two types of Immunizers according to the present invention.

The present invention therefore provides a vaccine for preventing viral infections comprising
an antigen, especially a viral antigen,
a peptide comprising a sequence $R_1$—$XZXZ_NXZX$—$R_2$, (SEQ ID NOS:1-5, wherein: xzxzzzxzx=SEQ ID NO:1; xzxzzzzxzx=SEQ ID NO:2; xzxzzzzzxzx=SEQ ID NO:3; xzxzzzzzzxzx=SEQ ID NO:4; xzxzzzzzzzxzx=SEQ ID NO:5) whereby N is a whole number between 3 and 7, preferably 5, X is a positively charged natural and/or non-natural amino acid residue, Z is an amino acid residue selected from the group consisting of L, V, I, F and/or W, and $R_1$ and $R_2$ are selected independently one from the other from the group consisting of —H, —$NH_2$, —$COCH_3$, —COH, a peptide with up to 20 amino acid residues or a peptide reactive group or a peptide linker with or without a peptide; X—$R_2$ may be an amide, ester or thioester of the C-terminal amino acid residue of the peptide (in the following also referred to as "Peptide A") and
an immunostimulatory oligodeoxynucleic acid molecule (ODN) having the structure according to the formula (I) wherein $$B-NUC-NMP_a-X_3-\overset{\overset{X_2}{\|}}{\underset{X_1}{P}}-X_4-CH_2-\underset{NMP_b-E}{\overset{R1}{\bigcirc}}$$

R1 is selected from hypoxanthine and uracile,
any X is O or S,
any NMP is a 2' deoxynucleoside monophosphate or monothiophosphate, selected from the group consisting of deoxyadenosine-, deoxyguanosine-, deoxyinosine-, deoxycytosine-, deoxyuridine-,
deoxythymidine-, 2-methyl-deoxyinosine-, 5-methyl-deoxycytosine-, deoxypseudouridine-, deoxyribosepurine-, 2-amino-deoxyribosepurine-, 6-S-deoxyguanine-, 2-dimethyl-deoxyguanosine- or N-isopentenyl-deoxyadenosine-monophosphate or -monothiophosphate;
NUC is a 2' deoxynucleoside, selected from the group consisting of deoxyadenosine-, deoxyguanosine-, deoxyinosine-, deoxycytosine-, deoxyinosine-, deoxythymidine-, 2-methyl-deoxyuridine-, 5-methyl-deoxycytosine-, deoxypseudouridine-, deoxyribosepurine-, 2-amino-deoxyribosepurine-, 6-S-deoxyguanine-, 2-dimethyl-deoxyguanosine- or N-isopentenyl-deoxyadenosine, a and b are integers from 0 to 100 with the proviso that a+b is between 4 and 150, and
B and E are common groups for 5' or 3' ends of nucleic acid molecules (in the following also referred to as "I-/U-ODN").

Of course, the present vaccine may further contain other substances, e.g. suitable pharmaceutically acceptable diluents or carrier, buffer or stabilising substances, etc.

The vaccine according to the present invention may further contain additional adjuvants, especially an Al(OH)$_3$ adjuvant (Alum).

Alum, as meant herein includes all forms of Al$^{3+}$ based adjuvants used in human and animal medicine and research. Especially, it includes all forms of aluminum hydroxide as defined in Römpp, 10th Ed. pages 139/140, gel forms thereof, aluminum phosphate, etc.

This is especially preferred for vaccines which are already on the market and contain such Al(OH)$_3$ adjuvants. In such a case, the combination of Immunizers according to the present invention may simply be added to such an existing vaccine.

The present antigen is preferably a viral antigen. If pronounced (or exclusive) Th1 type 1 responses should be specifically necessary, T cell epitopes (see introduction above) are preferred as antigens. Preferably the antigen is a viral antigen. In the example section the present invention is proven in principle and specifically effective with influenza and hepatitis viral antigens, namely with the hepatitis B surface antigen and hepatitis C antigens which are preferred antigens according to the present invention.

Of course, the pharmaceutical preparation may also comprise two or more antigens depending on the desired immune response. The antigen(s) may also be modified so as to further enhance the immune response.

Proteins or peptides derived from viral or bacterial pathogens, from fungi or parasites, as well as tumor antigens (cancer vaccines) or antigens with a putative role in autoimmune disease may be used as antigens (including derivatized antigens like glycosylated, lipidated, glycolipidated or hydroxylated antigens). Furthermore, carbohydrates, lipids or glycolipids may be used as antigens themselves. The derivatization process may include the purification of a specific protein or peptide from the pathogen, the inactivation of the pathogen as well as the proteolytic or chemical derivatization or stabilization of such a protein or peptide. Alternatively, also the pathogen itself may be used as an antigen. The antigens are preferably peptides or proteins, carbohydrates, lipids, glycolipids or mixtures thereof.

According to a preferred embodiment T cell epitopes are used as antigens. Alternatively, a combination of T cell epitopes and B cell epitopes may also be preferred.

Also mixtures of different antigens are of course possible to be used according to the present invention. Preferably, proteins or peptides isolated from a viral or a bacterial pathogen or from fungi or parasites (or their recombinant counterparts) are used as such antigens (including derivatized antigens or glycosylated or lipidated antigens or polysaccharides or lipids). Another preferred source of antigens are tumor antigens. Preferred pathogens are selected from human immunodeficiency virus (HIV), hepatitis A and B viruses, hepatitis C virus (HCV) or other Flaviviridae, such as Japanese encephalitis virus (JCV), rous sarcoma virus (RSV), Epstein Barr virus (EBV) Influenza virus, human papilloma virus (HPV), Rotavirus, *Staphylococcus aureus, Chlamydia pneumonias, Chlamydia trachomatis, Mycobacterium tuberculosis, Streptococcus pneumonias, Bacillus anthracis, Vibrio cholerae, Plasmodium* sp. (*Pl. falciparum, Pl. vivax*, etc.), *Aspergillus* sp. or *Candida albicans*.

In the case of peptide antigens the use of peptide mimotopes/agonists/superagonists/antagonists or peptides changed in certain positions without affecting the immunologic properties or non-peptide mimotopes/agonists/superagonists/antagonists is included in the current invention. Peptide antigens may also contain elongations either at the carboxy or at the amino terminus of the peptide antigen facilitating interaction with the polycationic compound(s) or the immunostimulatory compound(s).

Antigens may also be derivatized to include molecules enhancing antigen presentation and targeting of antigens to antigen presenting cells.

The Influenza or Hepatitis antigen to be used according to the present invention is not generally restricted to a specific form, it seems that the effect according to the present invention is even further pathogen-specifically enhanced for Influenza, Hepatitis B or Hepatitis C, but not specific for a certain type of antigen from this Influenza or HBV pathogen. However, it is preferred to use the standard Influenza or HBV antigens also in the present vaccines, i.e. a haemagglutinin antigen, a neuraminidase antigen, a combined antigen or a combination of one or more of these antigens.

Preferably, proteins or peptides isolated from an Influenza virus, HBV or HCV source (e.g. a cell culture) or their recombinant counterparts are used as such antigens, including derivatized antigens.

The vaccine according to the present invention preferably further (or, specifically in the case of Influenza, HCV or HBV, even instead of the Peptide A) contains a polycationic peptide.

The polycationic peptides or compound to be used according to the present invention may be any polycationic compound which shows the characteristic effect according to the WO 97/30721. Preferred polycationic compounds are selected from basic polypeptides, organic polycations, basic polyaminoacids or mixtures thereof. These polyaminoacids should have a chain length of at least 4 amino acid residues. Especially preferred are substances containing peptidic bounds, like polylysine, polyarginine and polypeptides containing more than 20%, especially more than 50% of basic amino acids in a range of more than 8, especially more than 20, amino acid residues or mixtures thereof. Other preferred polycations and their pharmaceutical compositions are described in WO 97/30721 (e.g. polyethyleneimine) and WO 99/38528. Preferably these polypeptides contain between 20 and 500 amino acid residues, especially between 30 and 200 residues.

These polycationic compounds may be produced chemically or recombinantly or may be derived from natural sources.

Cationic (poly)peptides may also be polycationic anti-bacterial microbial peptides. These (poly)peptides may be of prokaryotic or eukaryotic origin or may be produced chemically or recombinantly. Peptides may also belong to the class naturally occurring antimicrobial peptides. Such host defense peptides or defensives are also a preferred form of the polycationic polymer according to the present invention. Generally, a compound allowing as an end product activation (or down-regulation) of the adaptive immune system, preferably mediated by APCs (including dendritic cells) is used as polycationic polymer.

Furthermore, also neuroactive compounds, such as (human) growth hormone (as described e.g. in WO01/24822) may be used as immunostimulants (Immunizers).

Polycationic compounds derived from natural sources include HIV-REV or HIV-TAT (derived cationic peptides, antennapedia peptides, chitosan or other derivatives of chitin) or other peptides derived from these peptides or proteins by biochemical or recombinant production. Other preferred polycationic compounds are cathelin or related or derived substances from cathelicidin, especially mouse, bovine or especially human cathelicidins and/or cathelicidins. Related or derived cathelicidin substances contain the whole or parts of the cathelicidin sequence with at least 15-20 amino acid residues. Derivations may include the substitution or modification of the natural amino acids by amino acids which are not among the 20 standard amino acids. Moreover, further cationic residues may be introduced into such cathelicidin molecules. These cathelicidin molecules are preferred to be combined with the antigen/vaccine composition according to the present invention. However, these cathelin molecules surprisingly have turned out to be also effective as an adjuvants for a antigen without the addition of further adjuvants. It is therefore possible to use such cathelicidin molecules as efficient adjuvants in vaccine formulations with or without further immunoactivating substances.

The vaccine according to the present invention preferably contains as Peptide A KLKL$_5$KLK (SEQ ID NO: 6, which can also be written as KLKLLLLLKLK) and as I-/U-ODN oligo-d(IC)$_{13}$ (SEQ ID NO: 21; also referred to as o-d(IC)$_{13}$ or ODN1a). (The combination of Peptide A and oligo-d(IC)$_{13}$ is also referred as IC31). These two substances have shown specifically advantageous results in the experiments according to the present invention.

The vaccine according to the present invention may further (or, specifically in the case of Influenza, HCV or HBV; even instead of the U-/I-ODN) contain an oligodeoxynucleotide containing a CpG-motif as immunomodulating nucleic acids. The immunomodulating nucleic acids to be used according to the present invention can be of synthetic, prokaryotic and eukaryotic origin. In the case of eukaryotic origin, DNA should be derived from, based on the phylogenetic tree, less developed species (e.g. insects, but also others). In a preferred embodiment of the invention the immunogenic oligodeoxynucleotide (ODN) is a synthetically produced DNA-molecule or mixtures of such molecules. Derivates or modifications of ODNs such as thiophosphate substituted analogues (thiophosphate residues substitute for phosphate) as for example described in U.S. Pat. No. 5,723,335 and U.S. Pat. No. 5,663, 153, and other derivatives and modifications, which preferably stabilize the immunostimulatory composition(s) but do not change their immunological properties, are also included. A preferred sequence motif is a six base DNA motif containing an (unmethylated) CpG dinucleotide flanked by two 5' purines and two 3' pyrimidines (5'-Pur-Pur-C-G-Pyr-Pyr-3'). The CpG motifs contained in the ODNs according to the present invention are more common in microbial than higher vertebrate DNA and display differences in the pattern of methylation. Surprisingly, sequences stimulating mouse APCs are not very efficient for human cells. Preferred palindromic or non-palindromic ODNs to be used according to the present invention are disclosed e.g. in Austrian Patent applications A 1973/2000, A 805/2001, EP 0 468 520 A2, WO 96/02555, WO98/16247, WO 98/18810, WO 98/37919, WO 98/40100, WO 98/52581, WO 98/52962, WO 99/51259 and WO 99/56755 all incorporated herein by reference. ODNs/DNAs may be produced chemically or recombinantly or may be derived from natural sources. Preferred natural sources are insects.

The vaccine according to the present invention may preferably contain a polycationic peptide and an oligodeoxynucleotide containing a CpG-motif in combination. In the course of the present invention it has even turned out that the combination of CpG-ODN and polycationic peptide shows improvement effects in Influenza vaccine compositions, which are comparable to the effects of the combination of Peptide A and I-/U-ODNs and cannot only be combined with Peptide A and I-/U-ODNs but even be used instead of them. Of course, also mixtures of different immunostimulatory nucleic acids (I-/U-ODNs, CpG-ODNs, . . . ) and Peptide A variants (as well as other Immunizers) may be used according to the present invention.

According to another aspect, the present invention also relates to the use of a combination of Peptide A and a I-/U-ODN, both as defined according to the present invention, to improve the protective efficacy of a vaccine against a viral pathogen, especially influenza virus, HCV or HBV, HIV, HPV or JEV. Specifically, the antigen-specific type 1 response, especially IgG2-antibody response or IFN-gamma response, of a vaccine against a viral pathogen, especially influenza virus, HCV or HBV, HIV, HPV or JEV, can be improved and at the same time the type 2 response, especially IgG1-antibody response or interleukin 4 (IL 4) response, of said vaccine can be preserved or preferably also increased.

It has been shown previously (WO 02/13857) that naturally occurring, cathelicidin-derived antimicrobial peptides or derivatives thereof have an immune response stimulating activity and therefore constitute highly effective type 1 inducing adjuvants (Immunizers). Main sources of antimicrobial peptides are granules of neutrophils and epithelial cells lining the respiratory, gastro-intestinal and genitourinary tracts. In general they are found at those anatomical sites most exposed to microbial invasion, are secreted into internal body fluids or stored in cytoplasmic granules of professional phagocytes (neutrophils).

In the WO 02/32451 a type 1 inducing adjuvant (Immunizer) that is able to strongly enhance the immune response to a specific co-administered antigen and therefore constitutes a highly effective adjuvant is disclosed, Peptide A comprising a sequence R$_1$—XZXZ$_N$XZX—R$_2$. (SEQ ID NOS:1-5) A specifically preferred peptide is KLKLLLLLKLK (SEQ ID NO:6). Besides naturally occurring antimicrobial peptides, synthetic antimicrobial peptides have been produced and investigated. The synthetic antimicrobial peptide KLKLLLLLKLK-NH$_2$ (SEQ ID NO:6) was shown to have significant chemotherapeutic activity in *Staphylococcus aureus*-infected mice; human neutrophils were activated to produce the superoxide anion (O$_2^-$) via cell surface calreticulin. The exact number and position of K and L was found to be critical for the antimicrobial activity of the synthetic peptide (Nakajima, Y. (1997); Cho, J-H. (1999)).

The present invention is especially beneficial if the combined medicament is administered, e.g. subcutaneously, intramuscularly, intradermally or transdermally. However, other application forms, such as parenteral, intravenously, intranasally, oral or topical application, are also suitable for the present invention.

The Influenza antigen may be mixed with the adjuvant (Immunizer) (composition) according to the present invention or otherwise specifically formulated e.g. as liposome, retard formulation, etc.

The vaccines according to the present invention may be administered to an individual in effective amounts known to the skilled man in the art of Influenza vaccination. Optimization of antigen amount and Immunizer amount can be started from established amounts and using available methods.

The invention will be described in more detail by the following examples and figures, but the invention is of course not limited thereto.

Figure 5A:
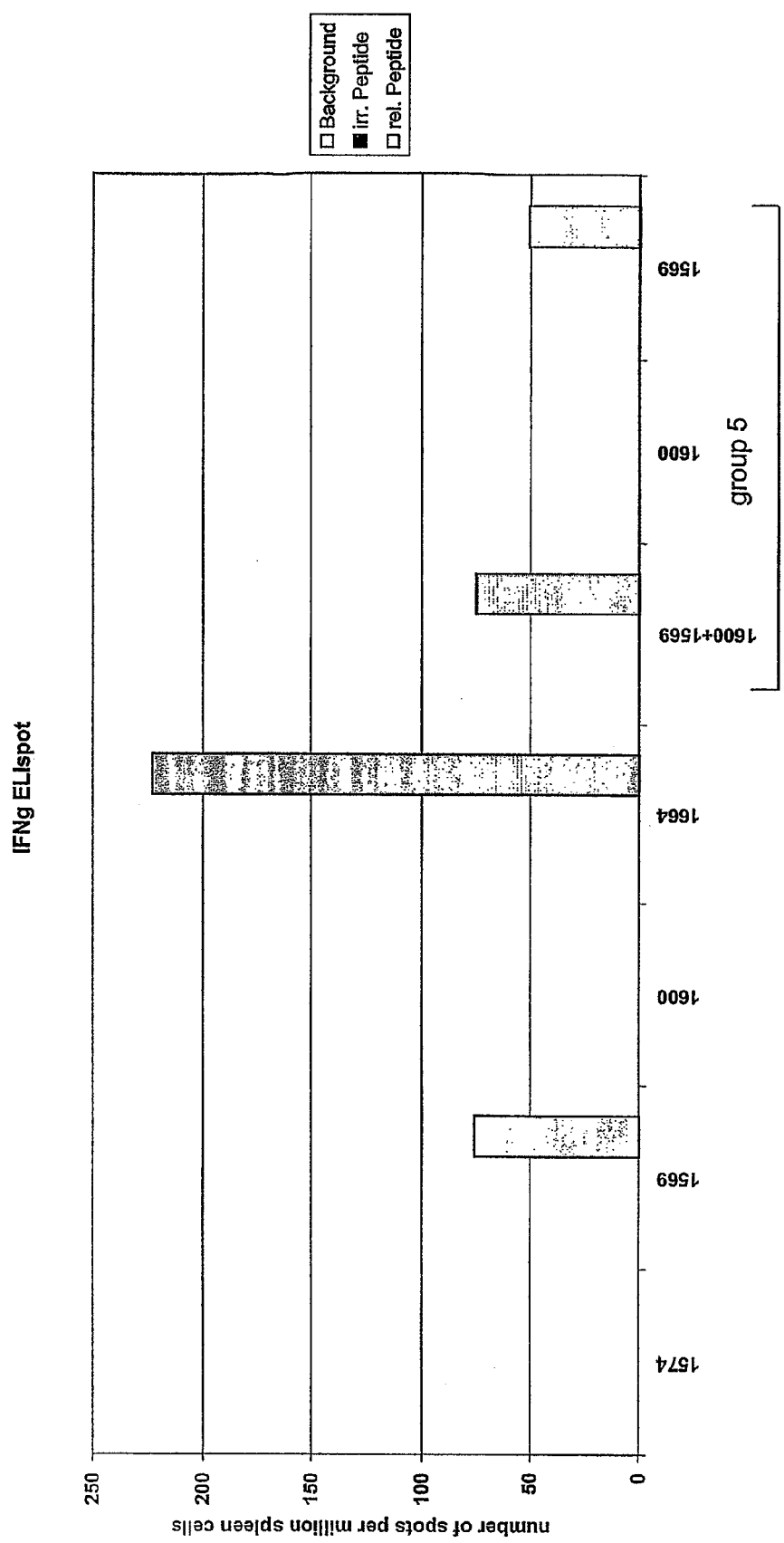
Figure 5B:
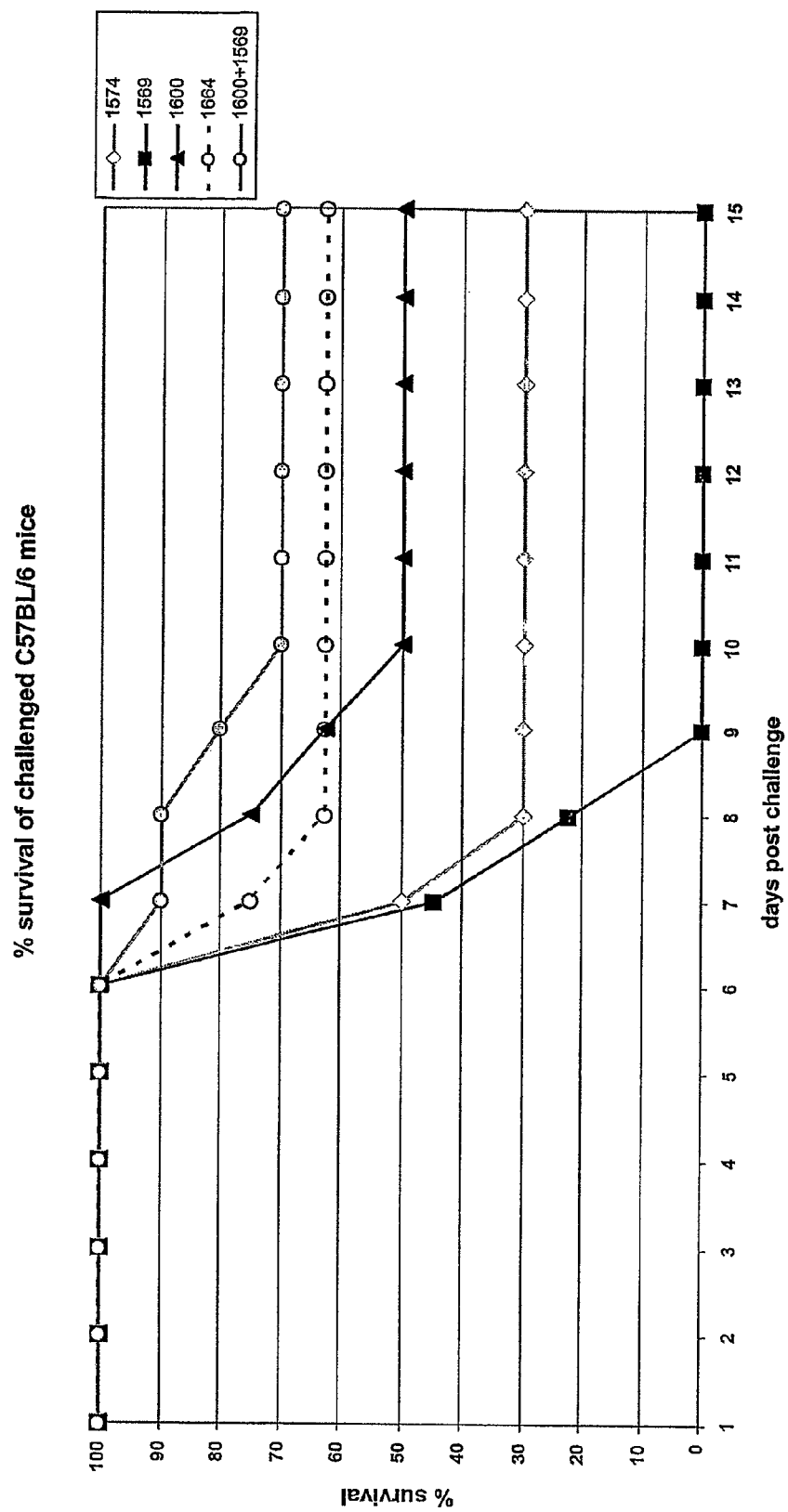
Figure 6:
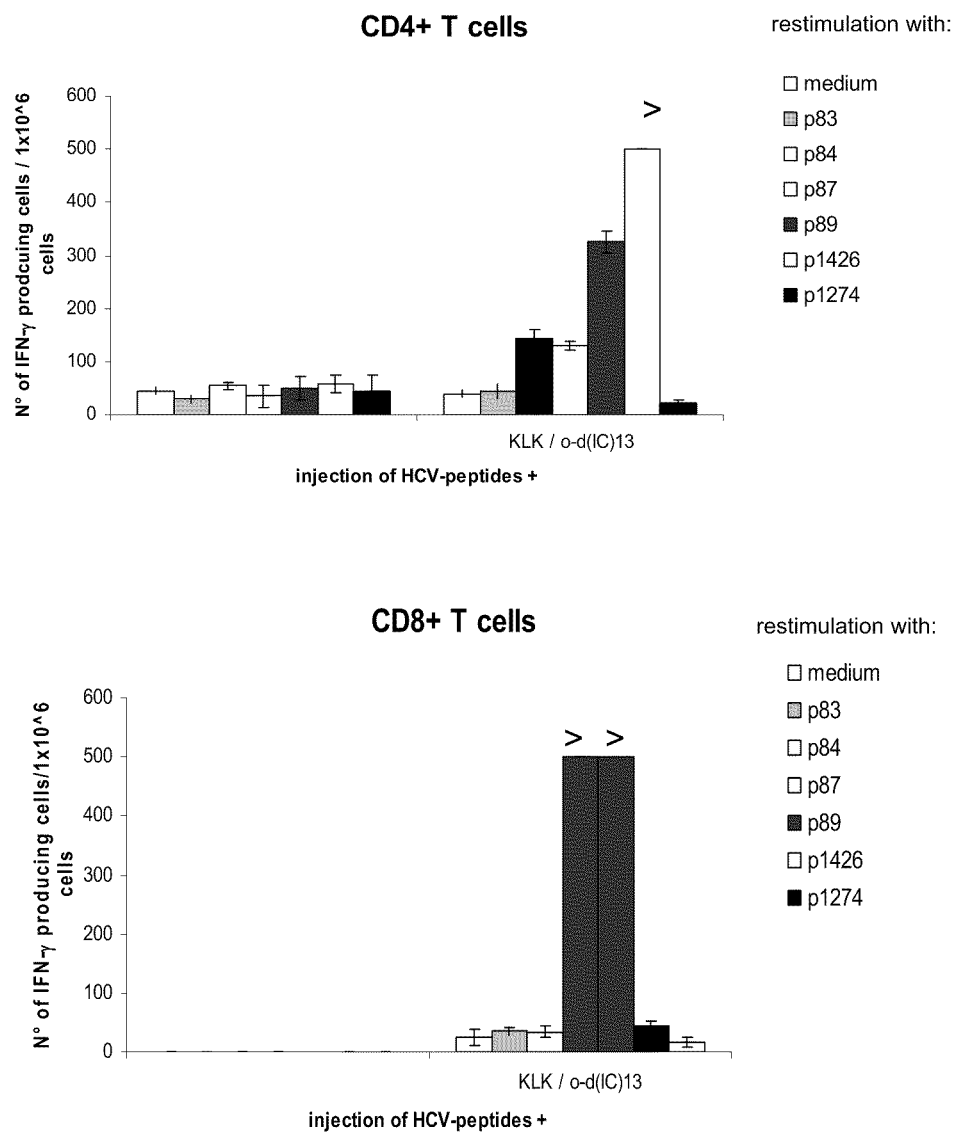
Figure 7:
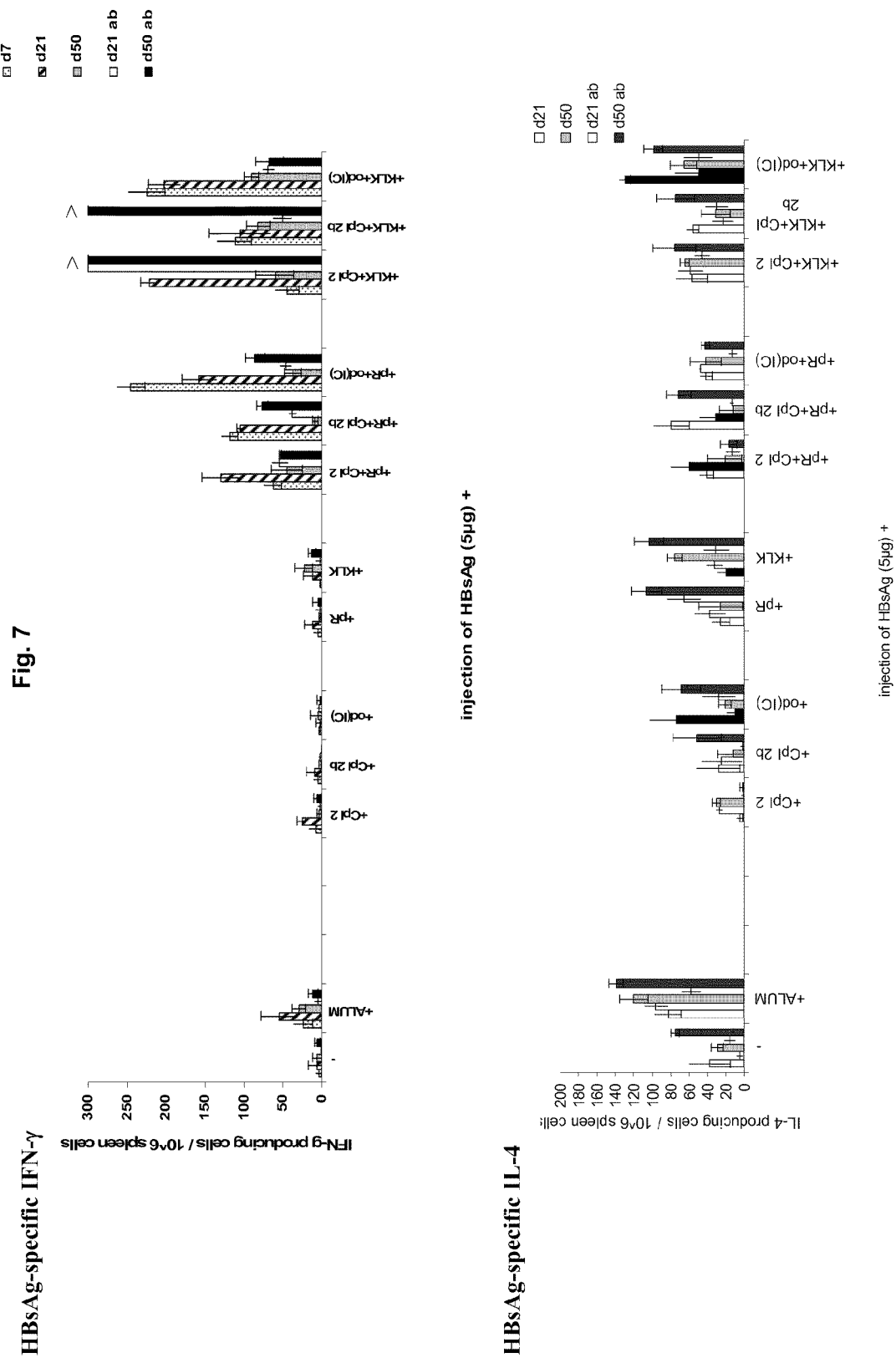

FIG. 3 shows that single injection of KLK/o-d(IC)$_{13}$ synergistically induces strong cellular type 1 and humoral type 1 and 2 responses against a commercially available Influenza vaccine FIG. 4 shows that single injection of KLK/o-d(IC)$_{13}$ strongly improves the efficacy of a commercially available Influenza vaccine FIG. 5 shows that vaccination with ncORF derived peptides from influenza A virus in combination with KLK/o-d(IC)$_{13}$ induces potent IFN-γ producing T cells and protection against viral challenge FIG. 6 shows that KLK/O-d(IC)$_{13}$ induces HCV-peptide specific type 1 cellular immune responses FIG. 7 shows that cationic peptides co-injected with different ODNs induce a HBsAg-specific cellular type 1 response (IFN-γ production) while the HBsAg-induced type 2 response (IL-4 production) is not affected or decreased.

Figure 8B:
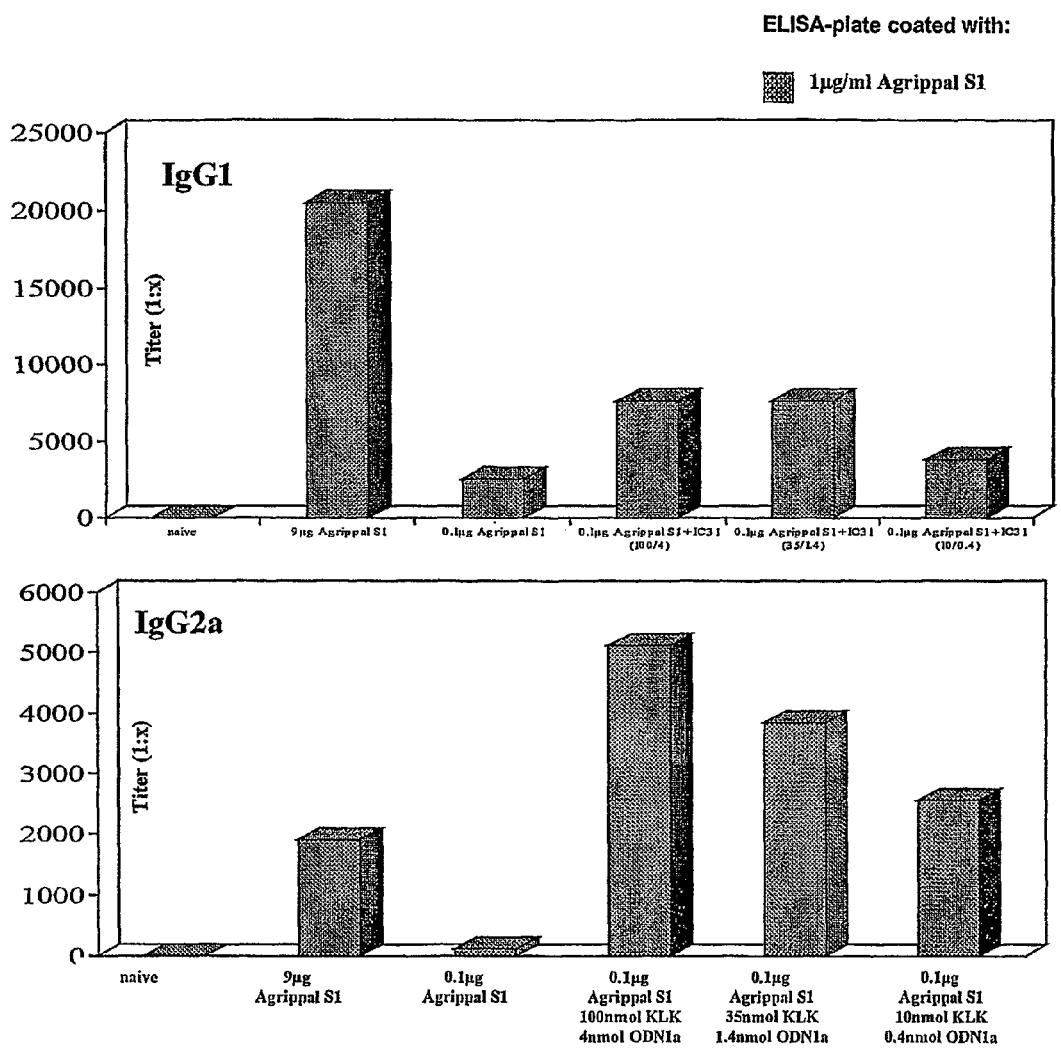

FIG. 8a shows the results of a single injection of the combination of the cationic antimicrobial peptide KLK with the synthetic oligodeoxynucleotide o-d(IC)13 (ODN1a) and low amounts of a commercially available influenza vaccine (Agrippal S1) synergistically induces strong vaccine specific cellular type I immune responses FIG. 8b shows the results of a single injection of the combination of the cationic antimicrobial peptide KLK with the synthetic oligodeoxynucleotide o-d(IC)13 (ODN1a) and a low amounts of a commercially available influenza vaccine (Agrippal S1) synergistically induces strong mixed type 1/type 2 humoral immune responses FIG. 9a: shows the results of a single injection of low dose of the combination of the cationic antimicrobial peptide KLK with the synthetic oligodeoxynucleotide o-d(IC)13 (ODN1a) synergistically induces strong cellular type immune responses against a commercially available influenza vaccine (Agrippal S1)

Figure 9B:
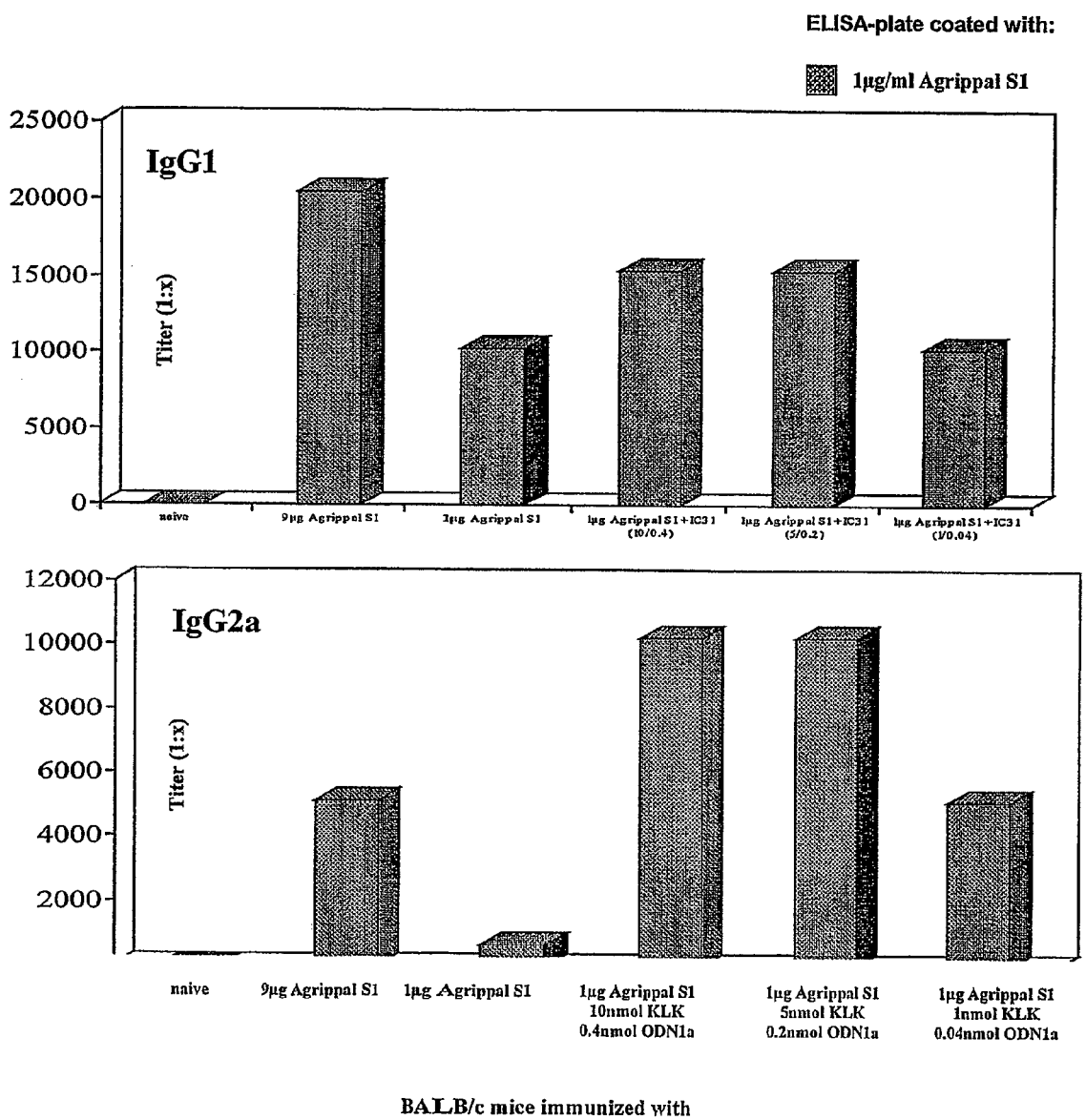
Figure 10:
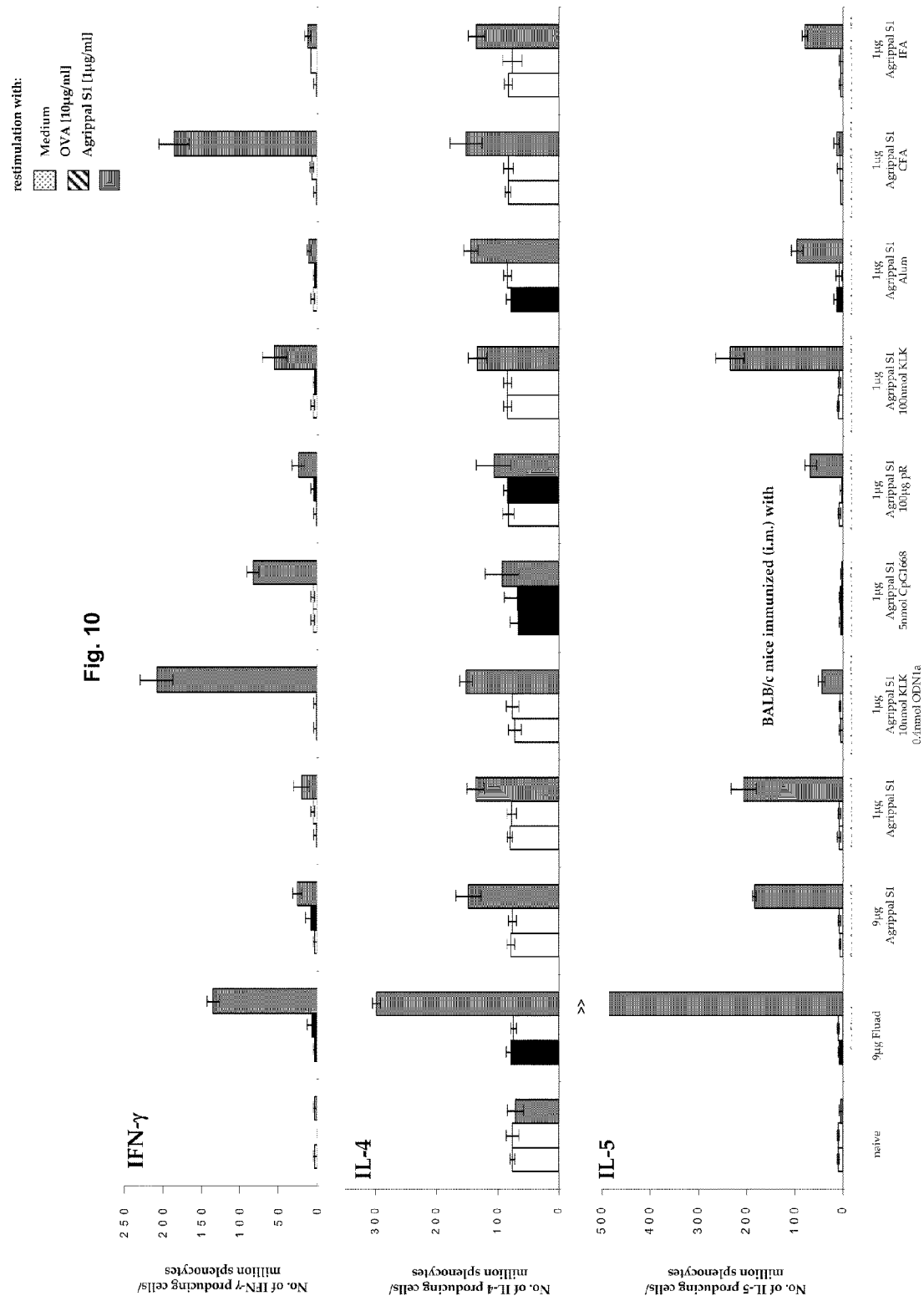

FIG. 9b: shows the results of a single injection of low dose of the combination of the cationic antimicrobial peptide KLK with the synthetic oligodeoxynucleotide o-d(IC)13 (ODN1a) and a low amounts of a commercially available influenza vaccine (Agrippal S1) synergistically induces strong mixed type 1/type 2 humoral immune responses FIG. 10 shows the results of a single injection of a commercially available influenza vaccine (Agrippal S1) combined with the cationic antimicrobial peptide KLK and the synthetic oligodeoxynucleotide o-d(IC)13 (ODN1a) compared to other adjuvants

EXAMPLES

Example 1

Cationic Peptides (pR or KLK) Co-Injected with Different Oligodeoxynucleotides (ODN) (CpI, ntCpI, o-d(IC)$_{13}$) Synergistically Induce Strong Type 1 Humoral Responses (IgG2b) Against a Commercially Available Influenza-Vaccine (Fluvirin)

Mice C57BL/6 (Harlan/Olac)
Influenza vaccine Fluvirin (Evans vaccine); inactivated Influenza virus surface antigens (haemagglutinin and neuraminidase) purified of strains:
  A/NewCaledonia/20/99 (H1N1)-like strain
    (15 µg haemagglutinin)
  A/Moscow/10/99 (H3N2)-like strain
    (A/Panama/2007/99 RESVIR-17)
    (15 µg haemagglutinin)
  B/Sichuan/379/99-like strain
    (15 µg haemagglutinin)
  dose: 1 µg total protein/mouse
Al(OH)$_3$ Alhydrogel; Biosys, Denmark
  dose: 1:1 mixture with antigen
pR Poly-L-Arginine with an average degree of polymerization of 43 arginine residues (determined by MALLS); Sigma Aldrich Inc
  dose: 100 µg/mouse
KLK KLKLLLLLKLK-COOH (SEQ ID NO:6) was synthesized by MPS (Multiple Peptide System, USA)
  dose: 168 µg/mouse
oligo-d(IC)$_{13}$ ODN1a (SEQ ID NO: 21) was synthesized by Purimex Nucleic Acids Technology, Göttingen
  dose: 5 nmol/mouse
I-ODN 2 a thiophosphate-substituted ODN containing deoxyinosine: tcc atg aci ttc ctg atg ct (SEQ ID NO: 22), was synthesized by Purimex Nucleic Acids Technology, Göttingen
  dose: 5 nmol/mouse
I-ODN 2b an ODN containing deoxyinosine: tcc atg aci ttc ctg atg ct (SEQ ID NO: 23), was synthesized by Purimex Nucleic Acids Technology, Göttingen
  dose: 5 nmol/mouse
formulation 5 mM Tris/270 mM Sorbitol, pH 7
Experimental Group (12 Mice/Group):
  1.: naïve
  2.: Flu vaccine
  3.: Flu vaccine+pR
  4.: Flu vaccine+KLK
  5.: Flu vaccine+Al(OH)$_3$
  6.: Flu vaccine+o-d(IC)$_{13}$
  7.: Flu vaccine+I-ODN 2
  8.: Flu vaccine+I-ODN 2b
  9.: Flu vaccine+pR+I-ODN 2
  10.: Flu vaccine+KLK+o-d(IC)$_{13}$
  11.: Flu vaccine+KLK+I-ODN 2
  12.: Flu vaccine+KLK+I-ODN 2b On days 0, 28 and 56 C57BL/6 mice were injected s.c. into both hind footpads with a total volume of 100 µl/mouse (50 µl/footpad) containing the above listed compounds. Serum was collected at days 26, 54 and 82 and analyzed for Influenza vaccine-specific IgG1 and IgG2b antibodies by ELISA. Titers correspond, to that dilution of serum resulting in half maximal OD$_{405nm}$.

Figure 1:
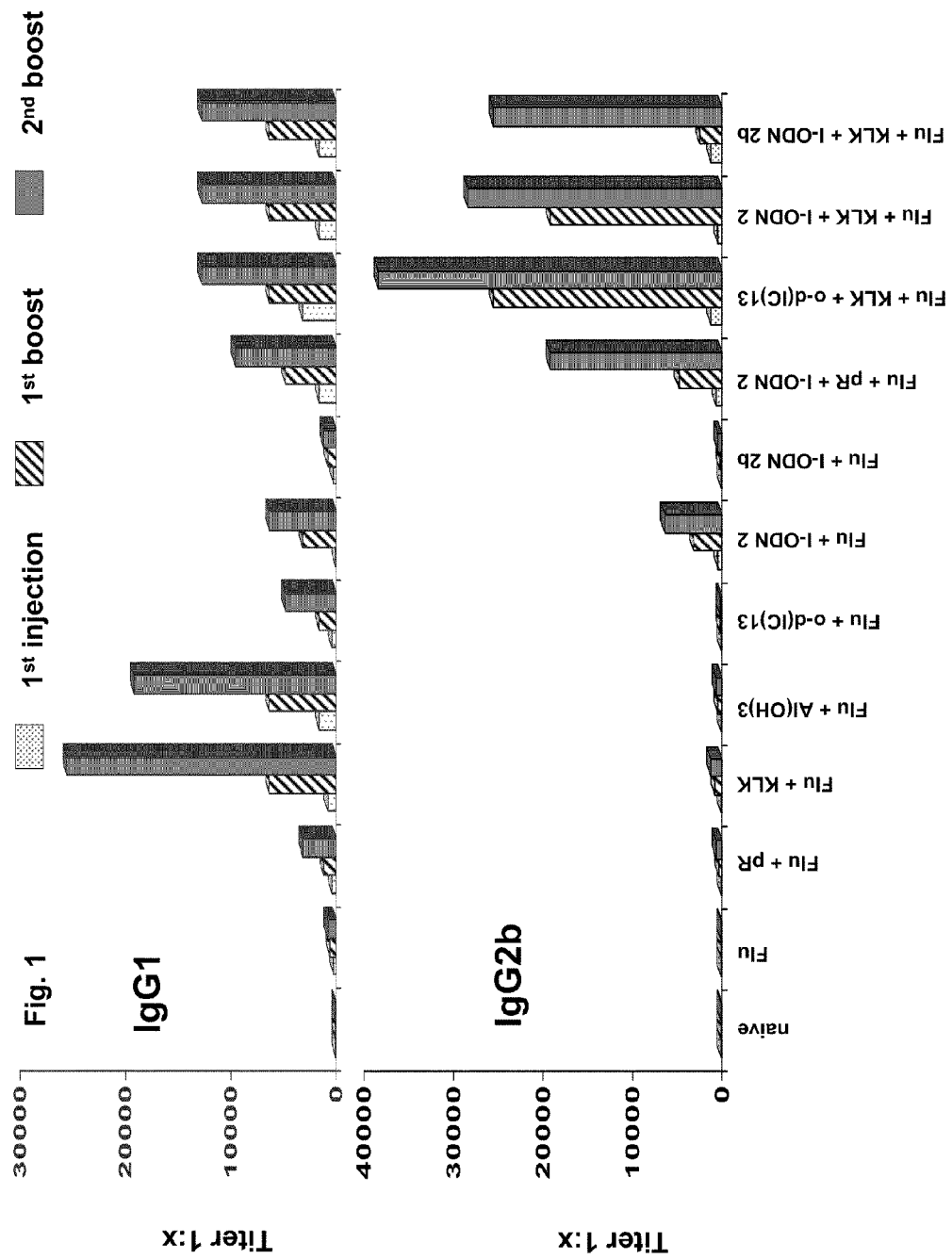
FIG. 1 shows that cationic peptides co-injected with different ODNs synergistically induce strong type 1 humoral responses (IgG2b) against a commercially available Influenza-vaccine.

FIG. 1 indicates that the combined injection of cationic peptides (pR or KLK) and different ODNs (I-ODN 2, I-ODN 2b, or o-d(IC)$_{13}$) induces very potent antigen (Influenza vaccine)-specific humoral type 1 responses (IgG2b) in a synergistic way. Upon injection of Influenza vaccine alone or in combination with Al(OH)$_3$, cationic peptides (pR, KLK) only or different ODNs (except I-ODN 2) only, no specific IgG2b response is detectable. Booster vaccinations strongly increase the observed response.

Co-injection of Influenza vaccine with Al(OH)$_3$, KLK or combinations pR/I-ODN 2, KLK/I-ODN 2, KLK/I-ODN 2b or KLK/o-d(IC)$_{13}$ induces the production of Influenza vaccine-specific IgG1 (type 2 response).

Example 2

The Combination KLK/o-d(IC)$_{13}$ Strongly Improves the Efficacy of a Commercially Available Influenza-Vaccine (Fluvirin)

Mice BALB/c (Harlan/Olac)
Influenza vaccine Fluvirin (Evans vaccine); inactivated Influenza virus surface antigens (haemagglutinin and neuraminidase) purified of strains:
  A/NewCaledonia/20/99 (H1N1)-like strain
    (15 µg haemagglutinin)
  A/Moscow/10/99 (H3N2)-like strain
    (A/Panama/2007/99 RESVIR-17)
    (15 µg haemagglutinin)
  B/Sichuan/379/99-like strain
    (15 µg haemagglutinin)
  dose: 1 µg total protein/mouse (=low dose/literature: 10 µg/mouse)
Al(OH)$_3$ Alhydrogel; Biosys, Denmark
  dose: 1:1 mixture with antigen
KLK KLKLLLLLKLK-COOH (SEQ ID NO:6) was synthesized by MPS (Multiple Peptide System, USA)
  dose: 168 µg/mouse
oligo-d(IC)$_{13}$ ODN1a (SEQ ID NO: 21) was synthesized by Purimex Nucleic Acids Technology, Göttingen
  dose: 5 nmol/mouse
formulation 5 mM Tris/270 mM Sorbitol, pH 7
Experimental Group (12 Mice/Group):
  1. naïve
  2. Flu vaccine
  3. Flu vaccine+Al(OH)$_3$
  4. Flu vaccine+KLK+o-d(IC)$_{13}$ On days 0, 28 and 56 BALB/c mice were injected s.c. into both hind footpads with a total volume of 100 µl/mouse (50 µl/footpad) containing the above listed compounds. Serum was collected at days 26, 54 and 82 and analyzed for neutralizing anti-haemagglutinin antibodies by using a standard haemagglutination inhibition assay. Briefly, the presence of haemagglutinin on the virus surface induces haemagglutination of erythrocytes, which can be inhibited by neutralizing anti-haemagglutinin antibodies. Titers of antibodies against haemagglutinin of the different viral strains (A1=A/New-Caledonia/20/99 (H1N1)-like strain; A2=A/Panama/2007/99 RESVIR-17; B=B/Sichuan/379/99-like strain) were determined. Titer of serum corresponds to end point dilution showing inhibition.

Figure 2:
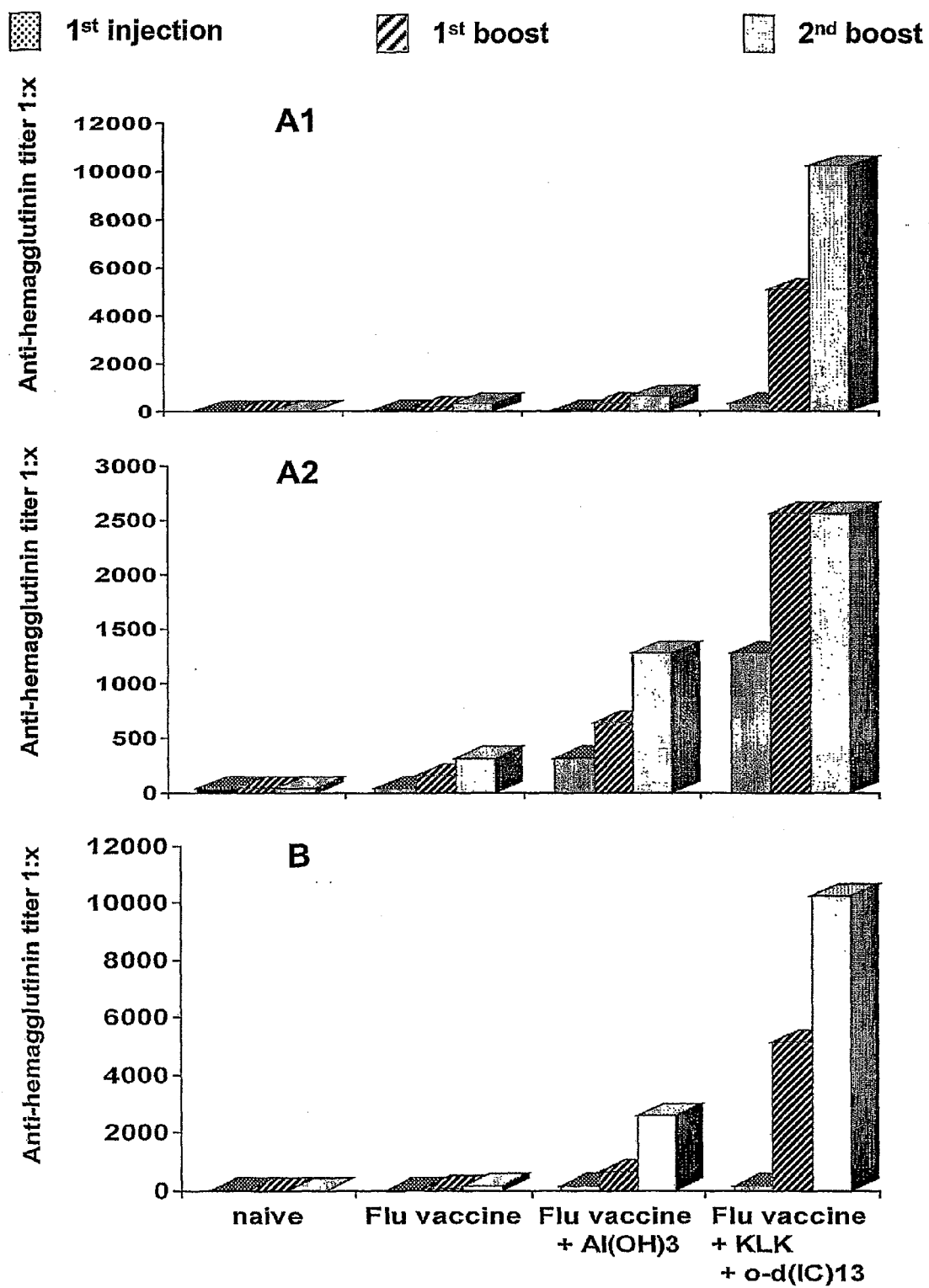
FIG. 2 shows that KLK/o-d(IC)$_{13}$ strongly improves the efficacy of a commercially available Influenza vaccine.

In contrast to injection of Influenza vaccine alone or in combination with Al(OH)$_3$ the co-injection of Influenza vaccine plus KLK and o-d(IC)$_{13}$ induces high levels of neutralizing antibodies against all three tested haemagglutinins (FIG. 2). Since effectiveness of an Influenza vaccine has been shown to correlate with serum titers of anti-haemagglutinin antibodies the obtained results indicate a high potential of KLK/o-d(IC)$_{13}$ for the induction of protection against Influenza.

Example 3

Single Injection of the Combination of the Cationic Antimicrobial Peptide KLK and the Synthetic Oligodeoxynucleotide o-d(IC)$_{13}$ Synergistically Induces Strong Cellular Type 1 and Humoral Type 1/Type 2 Immune Responses Against a Commercially Available Influenza Vaccine (Agrippal S1)

Materials
Mice BALB/c (Harlan-Winkelmann, Germany)
Influenza vaccines Agrippal S1 (Chiron SpA, Italy; season 2002/2003); inactivated purified influenza virus antigens (hemagglutinin and neuraminidase) from strains:
  A/New Caledonia/20/99 (H1N1)-like strain
    (A/New Caledonia/20/99 IVR-116)
  A/Moscow/10/99 (H3N2)-like strain
    (A/Panama/2007/99 RESVIR 17)
  B/Hong Kong/330/2001-like strain
    (B/Shangdong/7/97)
  Total antigen content: 45 µg (15 µg for each antigen); Lot #4307; expiry date May 2003
  Dose: 1 µg total protein mouse
Fluad (Chiron SpA, Italy; season 2002/2003); inactivated purified influenza virus antigens (hemagglutinin and neuraminidase) from strains:
  A/New Caledonia/20/99 (H1N1)-like strain
    (A/New Caledonia/20/99 IVR-116)
  A/Moscow/10/99 (H3N2)-like strain
    (A/Panama/2007/99 RESVIR 17)
    (B/Shangdong/7/97)
  Total antigen content: 45 µg (15 µg for each antigen); Addition of MF59C.1 as adjuvant
  Lot #3403; expiry date May 2003
  Dose: 1 µg total protein/mouse
oligo-d(IC)$_{13}$ ODN1a (SEQ ID NO: 21)
  synthesized by Purimex Nucleic Acids Technology, Göttingen
  Dose: 0.4 nmol/mouse
KLK KLKLLLLLKLK-COOH (SEQ ID NO:6) synthesized by MPS (Multiple Peptide System, USA)
  Dose: 10 nmol/mouse
Formulation 10 mM Tris/135 mM NaCl; pH ~7
Experimental Setup (10 Mice/Group)
  1. naïve
  2. Agrippal S1
  3. Fluad
  4. Agrippal S1+KLK+o-d(IC)$_{13}$ On day 0 BALB/c mice were injected intramuscularly into both hind femoral muscles with a total amount of 100 µl vaccine/mouse (50 µl/muscle) containing the above listed compounds. On day 21, serum was collected and analyzed for influenza vaccine-specific IgG1 and IgG2a antibodies by ELISA. Titers correspond to the dilution of serum resulting in half maximal OD405$_{nm}$. Furthermore, spleens of each experimental group were pooled and single cell suspensions were prepared. An aliquot of splenocytes was separated into CD4$^+$ T cells by magnetic sorting (CD4 MACS sort, Miltenyi). Either unseparated splenocytes or separated CD4$^+$ T cells in combination with irradiated antigen-presenting cells (APC; derived from naïve mice) were stimulated in 96-well ELIspot plates in order to enumerate the number of Agrippal S1 antigen-specific cytokine-producing cells for each experimental group. The production of following cytokines was analyzed:
  IFN-γ (as an indicator for a cellular type 1 response),
  IL-4 and IL-5 (as indicators for a cellular type 2 response)

Results (FIG. 3a)

Injection of low amounts of influenza vaccines Agrippal S1 (non-adjuvanted) and Fluad (MF59 adjuvanted) alone are not able to induce vaccine (Agrippal S1)-specific IFN-γ by CD4$^+$ T cells, whereas upon injection of Agrippal S1 in combination with KLK/o-d(IC)$_{13}$ a strong vaccine (Agrippal. S1)-specific IFN-γ production by CD4$^+$ T cells is observed. Compared to naïve mice, Agrippal S1 alone only slightly induces the production of IL-4 by CD4$^+$ T cells and the addition of KLK/o-d(IC)$_{13}$ to the vaccine shows no further increase. However, Fluad is a potent inducer of IL-4 production by CD4$^+$ T cells and IL-5 production by unseparated splenocytes. IL-5 is only detectable at very low levels upon injection of Agrippal S1 alone, but not in combination with KLK/o-d(IC)$_{13}$. Upon restimulation of unseparated splenocytes similar results are obtained Results (FIG. 3b)

FIG. 3b shows that the injection of the adjuvanted influenza vaccine Fluad alone induces a strong vaccine (Agrippal S1)-specific humoral type 2 response (IgG1), but only a weak type 1 response (IgG2a). However, the combined injection of the non-adjuvanted influenza vaccine with KLK/o-d(IC)$_{13}$ induces very potent vaccine (Agrippal S1)-specific IgG2a (humoral type 1 immune response) and higher levels of IgG1 than Agrippal S1 alone. Since protection against influenza is correlated with the presence of vaccine antigen-specific IgG2a antibodies, the obtained results indicate a high potential of KLK/o-d(IC)$_{13}$ as a potent adjuvant for influenza vaccines.

Example 4

The Combination KLK/o-d(IC)$_{13}$ Strongly Improves the Efficacy of a Commercially Available Influenza Vaccine (Agrippal S1) Upon Single Injection Materials
Mice BALB/c (Harlan-Winkelmann, Germany)
Influenza vaccines Agrippal S1 (Chiron SpA, Italy season 2002/2003); inactivated influenza virus antigens (hemagglutinin and neuraminidase) purified of strains:
  A/New Caledonia/20/99 (H1N1)-like strain
    (A/New Caledonia/20/99 IVR-116)
  A/Moscow/10/99 (H3N2)-like strain
    (A/Panama/2007/99 RESVIR 17)
  B/Hong Kong/330/2001-like strain
    (B/Shangdong/7/97)
  Total antigen content: 45 μg (15 μg for each antigen); Lot #4307; expiry date May 2003
  Dose: 1 μg total protein mouse
Fluad (Chiron SpA, Italy; season 2002/2003); inactivated influenza virus antigens (hemagglutinin and neuraminidase) purified of strains:
  A/New Caledonia/20/99 (H1N1)-like strain
    (A/New Caledonia/20/99 IVR-116)
  A/Moscow/10/99 (H3N2)-like strain
    (A/Panama/2007/99 RESVIR 17)
    (B/Shangdong/7/97)
  Total antigen content: 45 μg (15 μg for each antigen); Addition of MF59C.1 as adjuvant
  Lot #3403; expiry date May 2003
  Dose: 1 μg total protein/mouse
oligo-d(IC)$_{13}$ ODN1a (SEQ ID NO: 21)
  was synthesized by Purimex Nucleic Acids Technology, Göttingen
  Dose: 0.5 nmol/mouse
KLK KLKLLLLLKLK-COOH (SEQ ID NO:6)
  was synthesized by MPS (Multiple Peptide System, USA)
  Dose: 10 nmol/mouse
Formulation 10 mM Tris/270 mM Sorbit; pH ~7
Experimental Setup (10 Mice/Group)
  1. naïve
  2. Agrippal S1
  3. Fluad
  4. Agrippal S1+KLK+o-d(IC)$_{13}$ On day 0 BALB/c mice were injected intramuscularly into both hind femoral muscles with a total amount of 100 μl vaccine/mouse (50 μl/muscle) containing the above listed compounds. On day 21, serum was collected and analyzed for neutralizing anti-hemagglutinin antibodies by the use of a standard hemagglutinin inhibition (HI) assay for human sera. Titers of antibodies against hemagglutinin derived from different viral strains of both influenza vaccines Agrippal S1 and Fluad (see Materials) were determined.

Results (FIG. 4)

In contrast to injection of Agrippal S1 alone, the co-injection of the influenza vaccine with low amounts of KLK/o-d(IC)13 induces strongly increased levels of neutralizing antibodies against the two influenza A strains tested (A/New Caledonia/20/99; A/Panama/2007/99). However, immunization with Fluad induces the same levels of neutralizing antibodies as co-injection of Agrippal S1 with low amounts of KLK/o-d(IC)13. Since effectiveness of an influenza vaccine has been shown to correlate with serum titers of anti-hemagglutinin antibodies the present results indicate a high potential of KLK/o-d(IC)13 as an adjuvant for the induction of protection against influenza.

Example 5

Vaccination of Mice with ncORF Derived Peptides from Influenza A Virus in Combination with KLK/o-d(IC)$_{13}$. Specific T-Cell Response is Measured 7 Days after Vaccination, and Animals are Subsequently Challenged with a Lethal Dose of Mouse Adapted Influenza a Virus (x31). Survival is Monitored for 15 Days Materials
Mice C57Bl/6 (Harlan-Winkelmann, Germany)
Peptides p82 (GLCTLVAML) (SEQ ID NO:8)
  Control peptide derived from EBV; HLA-A*0201; AA start 280
p1574 (IASNENMETM) (SEQ ID NO:9)
  Control peptide derived from Influenza nucleoprotein, AA start 365
p1569 (TMLYNKMEF) (SEQ ID NO:10)
  Flu ncORF derived peptide from segment 1, frame 1, ORF 1, AA start 569
p1600 (SSIAAQDAL) (SEQ ID NO:11)
  Flu ncORF derived peptide from segment 3, frame 6, ORF 2, AA start 83
P1664 (VTILNLALL) (SEQ ID NO:12)
  Flu ncORF derived peptide from segment 4, frame 5, ORF 6, AA start 9
  Dose: 100 μg/peptide/mouse
o-d(IC)$_{13}$ (SEQ ID NO: 21)
  was synthesized by Purimex Nucleic Acids Technology, Göttingen
  Dose: 5 nmol/mouse
KLK KLKLLLLLKLK-COOH (SEQ ID NO:6)
  was synthesized by MPS (Multiple Peptide System, USA)
  Dose: 127 nmol/mouse Formulation 270 mM Sorbit/10 mM Hepes
Influenza A virus x31, mouse adapted influenza A virus, rec. virus derived from A/Pr/8/34 (seg 1, 2, 3, 5, 7, 8) and A/Aichi/2/68 (seg 4, 6)
Experimental Setup (15 Mice/Group)
1. p1574+KLK+o-d(IC)$_{13}$
2. p1569+KLK+o-d(IC)$_{13}$
3. p1600+KLK+o-d(IC)$_{13}$
4. p1664+KLK+o-d(IC)$_{13}$
5. p1600+p1569+KLK+o-d(IC)$_{13}$ On day 0 mice were injected s.c into both hind footpads with a total amount of 100 µl vaccine/mouse (50 µl/foot) containing the above listed compounds. On day 7, unseparated splenocytes from 5 mice were stimulated in 96-well ELIspot plates in order to enumerate the number of peptide-specific IFN-γ producing cells for each experimental group.

Remaining 10 mice were challenged with mouse adapted x31 influenza A virus (5*10E5 pfu). Survival was monitored for 15 days.

Results ELIspot (FIG. 5a)

Spleen cells of groups 1 and 3 (peptides p1574 and p1600) do not show any specific spots after restimulation with the respective peptides. Groups 2 and 4 (p1569 and p1664) specifically release IFN-γ after restimulation. Group 5 was vaccinated with two individual peptides (not as a mix, p1600 and p1569). Upon restimulation with either the mix of both peptides or p1569, specific cytokine release is detected. In contrast, upon restimulation with p1600 alone, no IFN-γ spots are detectable. This is consistent with group 3 (p1600 alone).

Results Challenge (FIG. 5b)

FIG. 5b shows the survival rate of challenged mice with a lethal dose of mice adapted influenza A virus x31. Group 1 (p1574, reported protective epitope for H2-Db) protects 30% of all challenged mice. Peptide p1569 does not at all provide protection (0%). In contrast, peptides p1600 and p1664 do protect 50% and 62% of challenged animals, respectively. When animals are vaccinated with two different peptides (group 5, peptides p1600 and 1569) up to 70% of animals are protected.

Example 6

Potent HCV-Specific Type 1 Cellular Responses are Induced by the Combined Injection of Five Different HCV-Derived Peptides, the Antimicrobial Peptide KLK and the Synthetic Oligodeoxynucleotide o-d(IC)$_{13}$ Mice HLA-A*0201 transgenic mice (HHD.1)
Peptides The peptides p83, p84, p87, p89, p1426 were used for vaccination.
  p83: HCV-derived peptide, (KFPGGGQIVGGVYLLPRRGPRL) (SEQ ID NO:13)
  p84: HCV-derived peptide, (GYKVLVLNPSVAAT) (SEQ ID NO:14)
  p87: HCV-derived peptide, (DLMGYIPAV) (SEQ ID NO:15)
  p89: HCV-derived peptide, (CINGVCWTV) (SEQ ID NO:16)
  p1426: HCV-derived peptide, HMWNFISGIQYLAGL-STLPGNPA) (SEQ ID NO:17)
  (p1274 used for restimulation as irrelevant peptide (YMDGTMSQV; HLA-A*0201 restricted) (SEQ ID NO:18)
All peptides were synthesized by standard solid phase F-moc synthesis, HPLC purified and analyzed by mass spectroscopy for purity.
  dose: 20 µg per peptide/mouse
KLKLLLLLKLK-COOH (SEQ ID NO:6) was synthesized by MPS (Multiple Peptide System, USA)
  dose: 10 nmol/mouse
oligo-d(IC)$_{13}$ ODN1a (SEQ ID NO: 21) was synthesized by Purimex Nucleic Acids Technology, Göttingen
  dose: 0.4 nmol/mouse
Formulation 10 mM Tris/135 mM NaCl; pH ~7
Experimental Setup (5 Mice/Group):
  1. HCV peptides
  2. HCV peptides+KLK+o-d(IC)$_{13}$ On days 0, 14 and 28 HHD.1 mice were injected s.c. into both hind footpads with a total volume of 100 µl/mouse (50 µl/footpad) containing the above listed compounds. At day 35 (7 days after last vaccination) CD4$^+$ as well as CD8$^+$ T cells were isolated by magnetic separation (MACS, Miltenyi) from single cell suspensions of spleen cells. T cells were incubated with medium (background control) or were restimulated with irradiated spleen cells from naïve HHD.1 mice as APC in the presence of either the different peptides used for vaccination or the irrelevant peptide p1274. After overnight incubation, the IFN-γ production was analyzed using an ELIspot assay.

FIG. 6 shows that upon co-injection of the five HCV-derived peptides with KLK/o-d(IC)$_{13}$ high amounts of IFN-□ produced by CD4$^+$ T cells against p84, p87, p89, p1426 were induced. Furthermore, a strong IFN-γ production by CD8$^+$ T cells against p87, p89 was detectable.

Example 7

Cationic Peptides (pR or KLK) Co-Injected with Different Oligodeoxynucleotides (ODN) (CpI, ntCpI, o-d(IC)$_{13}$) Synergistically Induce Strong Type 1 Cellular Responses (IFN-γ) Against Hepatitis B Surface Antigen Mice C57BL/6 (Harlan-Winkelmann, Germany); low responder mice for HbsAg-specific immune responses
Antigen Hepatitis B surface antigen (HBsAg)
  dose: 5 µg/mouse
Al(OH)$_3$ Alhydrogel; Biosys, Denmark
  dose: 1:1 mixture with antigen
pR Poly-L-Arginine with an average degree of polymerization of 43 arginine residues (determined by MALLS); Sigma Aldrich Inc
  dose: 100 µg/mouse
KLK KLKLLLLLKLK-COOH (SEQ ID NO:6) was synthesized by MPS (Multiple Peptide System, USA)
  dose: 168 µg/mouse
I-ODN 2 (SEQ ID NO: 22; also referred to as CpI 2), a thiophosphate-substituted ODN containing a deoxyinosine: 5'-tcc atg aci ttc ctg atg ct-3', was synthesized by Purimex Nucleic Acids Technology, Göttingen
  dose: 5 nmol/mouse
I-ODN 2b (SEQ ID NO: 23; also referred to as CpI 2b), an ODN containing a deoxyinosine: 5'-tcc atg aci ttc ctg atg ct-3', was synthesized by Purimex Nucleic Acids Technology, Göttingen
  dose: 5 nmol/mouse
o-d(IC)$_{13}$ ODN1a (SEQ ID NO: 21) was synthesized by Purimex Nucleic Acids Technology, Göttingen
  dose: 5 nmol/mouse
Formulation 5 mM Tris/270 mM Sorbitol, pH7
Experimental Setup (5 Mice/Group/Timepoint):
  1. HBsAg
  2. HBsAg+Alum
  3. HBsAg+I-ODN 2
  4. HBsAg+I-ODN 2b 5. HBsAg+o-d(IC)$_{13}$
6. HBsAg+pR
7. HBsAg+KLK
8. HBsAg+pR+I-ODN 2
9. HBsAg+pR+I-ODN 2b
10. HBsAg+pR+o-d(IC)$_{13}$
11. HBsAg+KLK+I-ODN 2
12. HBsAg+KLK+I-ODN 2b
13. HBsAg+KLK+o-d(IC)$_{13}$ On day 0 and day 56 mice were injected subcutaneously into the right flank with a total volume of 100 µl/mouse containing the above mentioned compounds. The analysis of the immune response was performed at day 7, day 21 and day 50 after first and second injection, respectively. Spleen cells of five mice per group per time point were restimulated ex vivo with 10 µg/ml HBsAg and ELIspot assays were performed in order to analyse the HBsAg-specific IFN-γ (type 1 immune response) as well as IL-4 (type 2 immune response) production.

Results (FIG. 7)

HBsAg injected alone or in combination with Alum induces no or only very low levels of IFN-γ, whereas upon injection of HBsAg combined with pR/ODN or KLK/ODN an HBsAg-specific IFN-γ production is induced which can be further increased, by booster vaccination. Slightly increased IL-4 production compared to injection of HBsAg alone is observable upon co-injection of Alum, pR and KLK after boost, as well upon co-injection of KLK/ODN combinations.

Example 8

Single injection of the combination of the cationic antimicrobial peptide KLK with the synthetic oligodeoxynucleotide o-d(IC)13 (ODN1a) and low amounts of a commercially available influenza vaccine (Agrippal S1) synergistically induces strong vaccine specific cellular type I immune responses Materials Mice BALB/c (Harlan-Winkelmann, Germany)

Influenza vaccine Agrippal S1 (Chiron SpA, Italy; vaccination season 2003/2004); lot 035105, expiry date June 2004
   Inactivated influenza virus antigens (haemagglutinin and neuraminidase) purified of strains:
      A/New Caledonia/20/99 (H1N1)-like strain (A/New Caledonia/20/99 IVR-116)
      A/Moscow/10/99 (H3N2)-like strain (A/Panama/2007/99 RESVIR 17)
      B/Hong Kong/330/2001-like strain (B/Shangdong/7/97)
   Total antigen content: 45 µg haemagglutinin (15 µg for each viral strain)
   Dose: 9 µg total protein/mouse (used directly from prefilled syringe) 0.1 µg total protein/mouse o-d(IC)$_{13}$ ODN1a (SEQ ID NO: 21); synthesized by Transgenomics; Part number: I02A03001N
   Dose: 4 nmol/mouse
      1.4 nmol/mouse
      0.4 nmol/mouse KLK synthetic cationic poly-amino acid containing lysine and leucine (KLKLLLLLKLK-COOH) (SEQ ID NO:6); synthesized by Bachem AG
Lot: 0562101;
Dose: 100 nmol/mouse
   35 nmol/mouse
   10 nmol/mouse Formulation by the Pharmaceutical Development Department at Intercell; 10 mM Tris/135 mM NaCl pH 7.5

Experimental Setup (10 Mice/Group)
1. naïve
2. 9 µg Agrippal S1
3. 0.1 µg Agrippal S1
4. 0.1 µg Agrippal S1+100 nmol KLK+4 nmol ODN1a
5. 0.1 µg Agrippal S1+35 nmol KLK+1.4 nmol ODN1a
6. 0.1 µg Agrippal S1+10 nmol KLK+0.4 nmol ODN1a On day 0, BALB/c mice were injected intramusculary into both femoral muscles with a total amount of 100 µl vaccine/mouse (50 µl/muscle) containing the above listed compounds. On day 21, serum was collected and analyzed for influenza vaccine-specific IgG1 and IgG2a antibodies by ELISA. Titers correspond to the dilution of serum resulting in half maximal OD405$_{nm}$. Furthermore, spleens of each experimental group were pooled and single cell suspensions were prepared. An aliquot of splenocytes was separated into CD4$^+$ and CD8$^+$ T cells by magnetic sorting (CD4 and CD8 MACS sort, Miltenyi). Either unseparated splenocytes or separated CD4$^+$ and CD8$^+$ T cells in combination with irradiated antigen-presenting cells (APC; derived from naïve mice) were stimulated in 96-well ELIspot plates in order to enumerate the number of Agrippal S1 antigen-specific cytokine-producing cells for each experimental group. The production of following cytokines was analyzed:
   IFN-γ (as an indicator for a cellular type 1 response),
   IL-4 and IL-5 (as indicators for a cellular type 2 response)

Results (FIG. 8a)

Vaccination of mice with 9 µg and 0.1 µg Agrippal S1 alone was not able to induce vaccine-specific IFN-γ by CD4$^+$ splenocytes, whereas upon injection of Agrippal S1 in combination with different concentrations of KLK/o-d(IC)$_{13}$ a strong IFN-γ production by CD4$^+$ splenocytes was observed. However, CD8$^+$ splenocytes were not able to induce IFN-γ. Compared to naïve mice, Agrippal S1 alone only slightly induced the production of IL-4 by unseparated and CD4$^+$ splenocytes and the addition of KLK/o-d(IC)$_{13}$ to the vaccine showed no further increase. However, Agrippal S1 induced IL-5 was totally abolished upon co-injection of KLK/o-d(IC)$_{13}$. Upon restimulation of unseparated splenocytes similar results are obtained.

Results (FIG. 8b)

As illustrated in FIG. 8b, the combined injection of low amounts of the non-adjuvanted influenza vaccine with different concentrations of KLK/o-d(IC)$_{13}$ induced very potent vaccine (Agrippal S1)-specific IgG2a (humoral type 1 immune response) and higher levels of IgG1 than low amounts of Agrippal. S1 alone. However, the high dose of Agrippal S1 showed the highest titers of vaccine-specific IgG1 antibodies. Since protection against influenza is correlated with the presence of vaccine antigen-specific IgG2a antibodies, the obtained results indicate a high potential of KLK/o-d(IC)$_{13}$ as a potent adjuvant for influenza vaccines.

Example 9

Single injection of low dose of the combination of the cationic antimicrobial peptide KLK with the synthetic oligodeoxynucleotide o-d(IC)13 (ODN1a) synergistically induces strong vaccine specific cellular type I immune responses against a commercially available influenza vaccine (Agrippal S1)

Materials

Mice BALB/c (Harlan-Winkelmann, Germany)

Influenza vaccine Agrippal S1 (Chiron SpA, Italy; vaccination season 2003/2004); lot 035105, expiry date June 2004
   Inactivated influenza virus antigens (haemagglutinin and neuraminidase) purified of strains:

A/New Caledonia/20/99 (H1N1)-like strain (A/New Caledonia/20/99 IVR-116)
A/Moscow/10/99 (H3N2)-like strain (A/Panama/2007/99 RESVIR 17)
B/Hong Kong/330/2001-like strain (B/Shangdong/7/97)
Total antigen content: 45 μg haemagglutinin (15 μg for each viral strain)
Dose: 9 μg total protein/mouse (used directly from pre-filled syringe) 1 μg total protein/mouse
o-d(IC)$_{13}$ ODN1a (SEQ ID NO: 21); synthesized by Trans-genomics; Part number: I02A03001N
Dose: 0.4 nmol/mouse
0.2 nmol/mouse
0.04 nmol/mouse
KLK synthetic cationic poly-amino acid containing lysine and leucine (KLKLLLLLKLK-COOH) (SEQ ID NO:6); synthesized by Bachem AG
Lot: 0562101;
Dose: 10 nmol/mouse
5 nmol/mouse
1 nmol/mouse
Formulation by the Pharmaceutical Development Department at Intercell; 10 mM Tris/135 mM NaCl pH 7.5
Experimental Setup (5 Mice/Group)
1. naïve
2. 9 μg Agrippal S1
3. 1 μg Agrippal S1
4. 1 μg Agrippal S1+10 nmol KLK+0.4 nmol ODN1a
5. 1 μg Agrippal S1+5 nmol KLK+0.2 nmol ODN1a
6. 1 μg Agrippal S1+1 nmol KLK+0.04 nmol ODN1a On day 0, BALB/c mice were injected intramusculary into both femoral muscles with a total amount of 100 μl vaccine/mouse (50 μl/muscle) containing the above listed compounds. On day 21, serum was collected and analyzed for influenza vaccine-specific IgG1 and IgG2a antibodies by ELISA. Titers correspond to the dilution of serum resulting in half maximal OD405$_{nm}$. Furthermore, spleens of each experimental group were pooled and single cell suspensions were prepared. Splenocytes were stimulated in 96-well ELIspot plates in order to enumerate the number of Agrippal S1 antigen-specific cytokine-producing cells for each experimental group. The production of following cytokines was analyzed:

IFN-γ (as an indicator for a cellular type 1 response),
IL-4 and IL-5 (as indicators for a cellular type 2 response)
Results (FIG. 9a)

Vaccination of mice with 9 μg and 1 μg Agrippal S1 alone was again (see also FIG. 8a) not able to induce vaccine-specific IFN-γ by murine splenocytes, whereas upon injection of Agrippal S1 in combination with different low concentrations of KLK/o-d(IC)$_{13}$ a strong IFN-γ production was observed. Compared to naïve mice, Agrippal S1 alone only slightly induced the production of IL-4 by murine splenocytes and the addition of KLK/o-d(IC)$_{13}$ to the vaccine had no effect. Agrippal S1 induced IL-5 was abolished upon co-injection of KLK/o-d(IC)$_{13}$ in a concentration dependent manner. Even at a very low dosage, the combination of KLK/o-d(IC)$_{13}$ induces a strong cellular type I immune responses.
Results (FIG. 9b)

The combined injection of low amounts of the non-adjuvanted influenza vaccine with different concentrations of KLK/o-d(IC)$_{13}$ induced very potent vaccine (Agrippal S1)-specific IgG2a (humoral type 1 immune response) and levels of IgG1 roughly comparable to low amounts of Agrippal S1 alone. However, the high dose of Agrippal S1 alone showed slightly increased titers of vaccine-specific IgG1 antibodies and comparable levels of IgG2a antibodies compared to co-injection of Agrippal S1 and the lowest concentration of KLK/o-d(IC)$_{13}$. Since protection against influenza is correlated with the presence of vaccine antigen-specific IgG2a antibodies, the obtained results indicate a high potential of KLK/o-d(IC)$_{13}$, even at a very low dosage, as a potent adjuvant for influenza vaccines.

Example 10

Single Injection of a Commercially Available Influenza Vaccine (Agrippal S1) Combined with the Cationic Antimicrobial Peptide KLK and the Synthetic Oligodeoxynucleotide o-d(IC)$_{13}$ (ODN1a) in Comparison to Other Adjuvants Materials
Mice BALB/c (Harlan-Winkelmann, Germany)
Influenza vaccines Agrippal S1 (Chiron SpA, Italy; vaccination season 2003/2004); lot 035105, expiry date June 2004 and
Fluad (Chiron SpA, Italy; vaccination season 2003/2004); lot 4003, expiry date May 2004; Addition of MF59C.1 as adjuvant
Both vaccines contain inactivated influenza virus antigens (haemagglutinin and neuraminidase) purified of strains:
A/New Caledonia/20/99 (H1N1)-like strain (A/New Caledonia/20/99 IVR-116)
A/Moscow/10/99 (H3N2)-like strain (A/Panama/2007/99 RESVIR 17)
B/Hong Kong/330/2001-like strain (B/Shangdong/7/97)
Total antigen content: 45 μg haemagglutinin (15 μg for each viral strain)
Dose: 9 μg total protein/mouse (used directly from pre-filled syringe) 1 μg total protein/mouse
o-d(IC)$_{13}$ ODN1a (SEQ ID NO: 21); synthesized by Trans-genomics; Part number: I02A03001N
Dose: 0.4 nmol/mouse
KLK synthetic cationic poly-amino acid containing lysine and leucine (KLKLLLLLKLK-COOH) (SEQ ID NO:6); synthesized by Bachem AG
Lot: 0562101;
Dose: 100 nmol/mouse
10 nmol/mouse
CpG1668 Thiophosphate-substituted ODN containing CpG motifs (5"-tcc atg acg ttc ctg atg ct-3"—SEQ ID NO:20); synthesized by Purimex Nucleic Acids Technology, Göttingen; lot. 020614
Dose: 5 nmol/mouse
Alum Al (OH)$_3$ [15 g/l]; provided by Chiron Behring, Germany
Dose: 1:1 mixture with antigen
pR Poly-L-Arginine with an average degree of polymerization of 43 arginine residues (determined by MALLS); provided by Sigma;
lot 50K7280;
Dose: 100 μg/mouse
IFA Incomplete Freud's Adjuvant; provided by Difco Lab.; lot. 2158430
Dose: 1:1 mixture with antigen
CFA Complete Freud's Adjuvant; provided by Difco Lab.; lot. 3126639
Dose: 1:1 mixture with antigen
Formulation by the Pharmaceutical Development Department at Intercell; 10 mM Tris/135 mM NaCl pH 7.5
Experimental Setup (5 Mice/Group)
1. naïve
2. 9 μg Fluad 3. 9 µg Agrippal S1
4. 1 µg Agrippal S1
5. 1 µg Agrippal S1+10 nmol KLK+0.4 nmol ODN1a
6. 1 µg Agrippal S1+5 nmol CpG1668
7. 1 µg Agrippal S1+100 µg pR43
8. 1 µg Agrippal S1+100 nmol KLK
9. 1 µg Agrippal S1+Alum
10. 1 µg Agrippal S1+CFA
11. 1 µg Agrippal S1+IFA On day 0, BALB/c mice were injected intramusculary into both femoral muscles with a total amount of 100 µl vaccine/mouse (50 µl/muscle) containing the above listed compounds. On day 21, spleens of each experimental group were pooled and single cell suspensions were prepared. Splenocytes were stimulated in 96-well ELIspot plates in order to enumerate the number of Agrippal S1 antigen-specific cytokine-producing cells for each experimental group. The production of following cytokines was analyzed:

IFN-γ (as an indicator for a cellular type 1 response),
IL-4 and IL-5 (as indicators for a cellular type 2 response)
Results (FIG. 10)

The combined injection of low amounts of the non-adjuvanted influenza vaccine with low doses KLK/o-d(IC)$_{13}$ induced higher levels vaccine (Agrippal S1)-specific IFN-γ by murine splenocytes compared to immunization with Agrippal S1 and Fluad alone. Comparable amounts of IFN-γ were only achieved upon vaccination with CFA, all other experimental groups showed roughly no (pR43, Alum, IFA) or a slightly increased (CpG1668, KLK) IFN-γ production by murine splenocytes compared to Agrippal S1 alone. In comparison to naïve mice, only Fluad markedly induced the production of IL-4 by murine splenocytes whereas all other experimental groups nearly showed the same low levels of IL-4. Vaccine antigen specific IL-5 was detectable at very high levels upon vaccination of mice with Fluad and at moderate levels upon injection of Agrippal S1 alone or in combination with KLK. Co-injection of Agrippal S1 with pR, Alum or IFA only slightly increased levels of IL-5, whereas all other groups showed a reduction in IL-5 production.

The invention claimed is:

1. A vaccine comprising:
   an HBV antigen;
   a peptide comprising the sequence KLKL$_5$KLK (SEQ ID NO: 6); and
   a deoxyinosine-containing immunostimulatory oligodeoxynucleic acid molecule (I-ODN), wherein the I-ODN comprises oligo-d(IC)$_{13}$ (SEQ ID NO: 21).

2. The vaccine of claim 1, further comprising an Al(OH)$_3$ adjuvant.

3. The vaccine of claim 1, wherein the HBV antigen is Hepatitis B surface antigen (HBsAg).

4. The vaccine of claim 1, further comprising a polycationic peptide.

5. The vaccine of claim 1, further comprising an oligodeoxynucleotide containing a CpG-motif.

6. The vaccine of claim 1, further comprising a polycationic peptide and an oligodeoxynucleotide containing a CpG-motif.

7. A method of improving protective efficacy of a vaccine against an HBV infection comprising:
   obtaining a peptide comprising the sequence KLKL$_5$KLK (SEQ ID NO: 6) and an I-ODN of claim 1, wherein the I-ODN comprises oligo-d(IC)$_{13}$ (SEQ ID NO: 21); and
   administering the peptide and the I-ODN with a vaccine against an HBV infection to a subject;
   wherein efficacy of the vaccine against an HBV infection is improved in the subject.

8. A method of improving an antigen-specific type 1 response of a vaccine against an HBV infection and preserving or increasing a type 2 response of said vaccine comprising:
   obtaining a peptide comprising the sequence KLKL$_5$KLK (SEQ ID NO: 6) and an I-ODN of claim 1, wherein the I-ODN comprises oligo-d(IC)$_{13}$ (SEQ ID NO: 21); and
   administering the peptide and the I-ODN with a vaccine against an HBV infection to a subject;
   wherein the antigen-specific type 1 response to the vaccine against an HBV infection is improved in the subject and the type 2 response to the vaccine is preserved or increased in the subject.

9. A immunogenic composition comprising:
an HCV antigen,
a peptide comprising the sequence KLKL$_5$KLK (SEQ ID NO: 6), and
a deoxyinosine-containing immunostimulatory oligodeoxynucleic acid molecule (I-ODN), wherein the I-ODN comprises oligo-d(IC)$_{13}$ (SEQ ID NO: 21).

10. The immunogenic composition of claim 9, further comprising an Al(OH)$_3$ adjuvant.

11. The immunogenic composition of claim 9, wherein the HCV antigen is a peptide.

12. The immunogenic composition of claim 9, further comprising a polycationic peptide.

13. The immunogenic composition of claim 9, further comprising an oligodeoxynucleotide containing a CpG-motif.

14. The immunogenic composition of claim 9, further comprising a polycationic peptide and an oligodeoxynucleotide containing a CpG-motif.

15. A method of improving efficacy of a immunogenic composition against an HCV infection comprising:
obtaining a peptide comprising the sequence KLKL$_5$KLK (SEQ ID NO: 6) and an I-ODN of claim 9, wherein the I-ODN comprises oligo-d(IC)$_{13}$ (SEQ ID NO: 21); and
administering the peptide and the I-ODN with a immunogenic composition against an HCV infection to a subject;
wherein efficacy of the immunogenic composition against HCV infection is improved in the subject.

16. A method of improving an antigen-specific type 1 response of a immunogenic composition against an HCV infection and preserving or increasing a type 2 response of said immunogenic composition comprising:
obtaining a peptide comprising the sequence KLKL$_5$KLK (SEQ ID NO: 6) and an I-ODN of claim 9, wherein the I-ODN comprises oligo-d(IC)$_{13}$ (SEQ ID NO: 21); and
administering the peptide and the I-ODN with a immunogenic composition against an HCV infection to a subject;
wherein the antigen-specific type 1 response to the immunogenic composition against an HCV infection is improved in the subject and the type 2 response to the immunogenic composition is preserved or increased in the subject.

17. The method of claim 8 or 16, wherein the antigen-specific type 1 response is further defined as an IgG2-antibody response or IFN-gamma response.

18. The method of claim 8 or 16, where in the type 2 response is further defined as an IgG1-antibody response or interleukin-4 (IL-4) response.

* * * * *

UNITED STATES PATENT AND TRADEMARK OFFICE
CERTIFICATE OF CORRECTION

PATENT NO. : 8,784,837 B2
APPLICATION NO. : 12/759318
DATED : July 22, 2014
INVENTOR(S) : Michael Buschle et al.

It is certified that error appears in the above-identified patent and that said Letters Patent is hereby corrected as shown below:

In the Claims:

Claim 9, starting at column 31, lines 1-7 should read:

9. An immunogenic composition comprising:

an HCV antigen, a peptide comprising the sequence KLKL$_5$KLK (SEQ ID NO: 6), and a deoxyinosine-containing immunostimulatory oligodeoxynucleic acid
molecule (I-ODN), wherein the I-ODN comprises oligo-d(IC)$_{13}$ (SEQ ID NO: 21).

Claim 15, starting at column 31, lines 19 - column 32, lines 1-2 should read:

15. A method of improving efficacy of an immunogenic composition against an HCV infection comprising:
obtaining a peptide comprising the sequence KLKL$_5$KLK (SEQ ID NO: 6)
and an I-ODN of claim 9, wherein the I-ODN comprises oligo-d(IC)$_{13}$ (SEQ ID NO: 21); and
administering the peptide and the I-ODN with an immunogenic composition
against an HCV infection to a subject;
wherein efficacy of the immunogenic composition against HCV infection is improved in the subject.

Signed and Sealed this
Thirty-first Day of May, 2016

Michelle K. Lee
*Director of the United States Patent and Trademark Office*

CERTIFICATE OF CORRECTION (continued)
U.S. Pat. No. 8,784,837 B2

In the Claims:

Claim 16, starting at column 32, lines 3-18 should read:

16. A method of improving an antigen-specific type 1 response of an immunogenic composition against an HCV infection and preserving or increasing a type 2 response of said immunogenic composition comprising:

obtaining a peptide comprising the sequence $KLKL_5KLK$ (SEQ ID NO: 6) and an I-ODN of claim 9, wherein the I-ODN comprises oligo-$d(IC)_{13}$ (SEQ ID NO: 21); and administering the peptide and the I-ODN with an immunogenic composition against an HCV infection to a subject;

wherein the antigen-specific type 1 response to the immunogenic composition against an HCV infection is improved in the subject and the type 2 response to the immunogenic composition is preserved or increased in the subject.